(12) United States Patent
Tang

(10) Patent No.: US 9,254,472 B2
(45) Date of Patent: Feb. 9, 2016

(54) PROCESS AND APPARATUS FOR SUPERSONIC COLLISION SHOCKWAVE REACTION MECHANISM FOR MAKING CHEMICAL COMPOUNDS

(71) Applicant: Physical Shockwave Industrial Applications, LLC, Frisco, TX (US)

(72) Inventor: Robert E. Tang, Dallas, TX (US)

(73) Assignee: Physical Shockwave Industrial Applications, LLC, Frisco, TX (US)

( * ) Notice: Subject to any disclaimer, the term of this patent is extended or adjusted under 35 U.S.C. 154(b) by 48 days.

(21) Appl. No.: 14/052,444

(22) Filed: Oct. 11, 2013

(65) Prior Publication Data

US 2014/0121346 A1 May 1, 2014

Related U.S. Application Data

(60) Provisional application No. 61/720,919, filed on Oct. 31, 2012.

(51) Int. Cl.
*B01J 19/10* (2006.01)
*C07D 301/22* (2006.01)
(Continued)

(52) U.S. Cl.
CPC .............. *B01J 19/10* (2013.01); *B01F 5/0256* (2013.01); *B01F 13/1016* (2013.01); *B01J 3/08* (2013.01); *B01J 4/002* (2013.01); *C07C 1/0495* (2013.01); *C07C 1/12* (2013.01); *C07C 17/26* (2013.01); *C07C 29/152* (2013.01); *C07C 29/159* (2013.01); *C07C 29/32* (2013.01);
(Continued)

(58) Field of Classification Search
CPC ...... B01J 19/10; C07C 29/152; C07C 29/159; C07C 1/0495; C07D 301/22; C07D 301/04; C08F 114/06
See application file for complete search history.

(56) References Cited

U.S. PATENT DOCUMENTS 3,185,740 A 5/1965 Malick
3,307,917 A 3/1967 Hansel et al.
(Continued)

FOREIGN PATENT DOCUMENTS

| CN | 102531827 A | * | 7/2012 |
| FR | 2619320 | | 2/1989 |
| WO | 2012/041229 | | 4/2012 |

OTHER PUBLICATIONS

CN 102531827 A, Jul. 2012, pp. 1-4; English translation.*
(Continued)

*Primary Examiner* — Fereydoun G Sajjadi
*Assistant Examiner* — Medhanit Bahta
(74) *Attorney, Agent, or Firm* — Jackson Walker L.L.P.

(57) ABSTRACT

A novel process and apparatus is disclosed for performing chemical reactions. Highly compressed gaseous streams such as $H_2$, $CO$, $CO_2$, $H_2O$, $O_2$, or $CH_4$ are raised to Mach speeds to form supersonic jets incorporating shockwaves. Two or more such jets are physically collided together to form a localized reaction zone where the energy from the shockwaves causes endothermic reactions wherein the chemical bonds of the reactant gases are broken. Between and among reactants molecular surface interaction and molecular surface chemistry take place. In the ensuing exothermic reactions a desired new chemical product is formed and this product is locked into a lower state of enthalpy (state of energy of formation) through adiabatic cooling by means of a free jet expansion.

18 Claims, 14 Drawing Sheets

(51) Int. Cl.

| | | |
|---|---|---|
| C08F 114/06 | (2006.01) | |
| C07C 29/159 | (2006.01) | |
| C07C 1/04 | (2006.01) | |
| C07C 1/12 | (2006.01) | |
| C07C 29/152 | (2006.01) | |
| C07D 301/04 | (2006.01) | |
| C07C 29/32 | (2006.01) | |
| C07C 29/34 | (2006.01) | |
| C07C 17/26 | (2006.01) | |
| C07D 301/10 | (2006.01) | |
| B01J 3/08 | (2006.01) | |
| B01J 4/00 | (2006.01) | |
| B01F 5/02 | (2006.01) | |
| B01F 13/10 | (2006.01) | |

(52) U.S. Cl.
CPC .......... *C07C 29/34* (2013.01); *C07D 301/04* (2013.01); *C07D 301/10* (2013.01); *C07D 301/22* (2013.01); *C08F 114/06* (2013.01)

(56) References Cited

U.S. PATENT DOCUMENTS

| | | |
|---|---|---|
| 4,272,463 A | 6/1981 | Clark et al. |
| 4,909,914 A | 3/1990 | Chiba et al. |
| 6,682,705 B1 * | 1/2004 | Gross et al. .................. 422/139 |
| 6,706,770 B2 | 3/2004 | Patel et al. |
| 7,842,264 B2 | 11/2010 | Cooper et al. |
| 2003/0153709 A1 | 8/2003 | Marcarian et al. |
| 2010/0190874 A1 * | 7/2010 | Mamedov et al. ............ 518/702 |

OTHER PUBLICATIONS

Tang, R. E. "High-Value Beneficial By-Products from Coal Combustion and Gasification at Ultra-Low Cost Inputs through Innovative Technology", Jul. 26, 2012, pp. 1-17.*

Tepermeister, I. et al. "Methane to methanol: reactor design and process evaluation" 1988, pp. 1-115.*

European Patent Office; Response to Written Opinion and Demand; PCT Application No. PCT/US2013/064653; Nov. 17, 2014.

European Patent Office; Second Written Opinion; PCT Application No. PCT/US2013/064653; Jan. 23, 2015.

European Patent Office; First Response to Second Written Opinion; PCT Application No. PCT/US2013/064653; Feb. 13, 2015.

European Patent Office; Second Response to Second Written Opinion; PCT Application No. PCT/US2013/064653; Mar. 10, 2015.

European Patent Office; International Preliminary Report on Patentability; PCT Application No. PCT/US2013/064653; Mar. 27, 2015.

European Patent Office; Invitation to Pay Additional Fees; PCT Application No. PCT/US2013/064653; Jul. 1, 2014.

European Patent Office; International Search Report and Written Opinion; PCT Application No. PCT/US2013/064653; Sep. 2, 2014.

* cited by examiner

A.

B.

A.

B.

A.

B.

PROCESS AND APPARATUS FOR SUPERSONIC COLLISION SHOCKWAVE REACTION MECHANISM FOR MAKING CHEMICAL COMPOUNDS

This application claims priority to U.S. Provisional Patent Application No. 61/720,919 entitled "Process and Apparatus for Supersonic Collision Shockwave Reaction Mechanism for Making Chemical Compounds," filed Oct. 31, 2012, the entire contents of which is hereby incorporated by reference.

BACKGROUND

This disclosure relates generally to the field of chemical compound production and more specifically to an improved process and apparatus for using the extremely time-efficient, energy input-efficient, and therefore cost-efficient "collision physics" to achieve chemical compound production by means of the supersonic collision shockwave reaction mechanism.

For centuries, the conventional way of chemical reaction was based on mixing two or more chemicals in a stirring, blending or intermixing method with or without the addition of a liquid, often with the assistance of the input of heat, pressure and time, and sometimes further assisted by introducing a catalyst into the reaction. The objective was to cause the original respective bonding of a chemical A and a different chemical B to be loosened, thereby to allow one or more new compounds to be made as a result of a new pairing of A and B. If either or both of A and B are themselves compounds, then a new pairing of a number of variations of the components of A and B.

Methanol Production as an Example

Low carbon alcohols have been produced from a variety of feedstocks, including wood, biomass, methane ($CH_4$) and synthesis gas. Centuries ago, methanol, then known as "pyroxylic spirit", was produced by the pyrolysis of wood. Methanol is the simplest alcohol. Originally, synthesis gas for the production of methanol came from coal. In 1923, the German chemists Alwin Mittasch and Mathias Pier at BASF developed a method to convert primarily from coal and petroleum feedstock a mixture of carbon monoxide (CO), carbon dioxide ($CO_2$), and hydrogen ($H_2$) into methanol ($CH_3OH$). BASF in 1926 obtained U.S. Pat. No. 1,569,775 for a process to manufacture methanol from carbon monoxide and hydrogen in the presence of a catalyst "free from iron" where the improvement consisted of completely excluding iron from the reaction. The BASF process used a chromium and manganese oxide catalyst at pressures ranging from 50 to 220 atmospheres (735 psig to 3,200 psig) and temperatures ranging from 482° F. to 1,112° F. (250° C. to 600° C.).

Coal gasification is a chemical process that is used to convert coal to carbon monoxide gas and hydrogen gas. The mixture of carbon monoxide gas and hydrogen gas is called synthesis gas (also generally referred to as "syngas"). In the 1920s two German researchers named Franz Fischer and Hans Tropsch invented a catalyzed chemical reaction process (the Fischer-Tropsch process) in which carbon monoxide gas and hydrogen gas may be converted into liquid hydrocarbons of various forms. Typical catalysts that are used in the process are based on iron and cobalt. The principal purpose of the process is to produce a synthetic petroleum substitute for use as synthetic lubrication oil or as synthetic fuel.

The original Fischer-Tropsch process for "Syngas" reformation (Eq. 1) and for alkane formation (Eq. 2) is described by the following chemical equations:

$$CH_4 + 0.5O_2 \rightarrow 2H_2 + CO + \text{Heat} \tag{Eq. 1}$$

$$(2n+1)H_2 + nCO \rightarrow C_nH_{(2n+2)} + nH_2O \tag{Eq. 2}$$

The step that is described in Equation 1 is the coal gasification process from methane feedstock. The step that is described in Equation 2 is the Fischer-Tropsch liquefaction process. Liquefaction is the change of a substance from a solid or gaseous state to a liquid state. The utility of the Fischer-Tropsch process is primarily in its role in producing fluid hydrocarbons or hydrogen from a solid feedstock such as coal or solid carbon-containing waste. It is well known that non-oxidative pyrolysis of the solid material produces syngas which can be used directly or as a fuel without being taken through the Fischer-Tropsch process. If liquid petroleum-like fuel, lubricant or wax is desired, the Fischer-Tropsch process may be applied.

In recent years, advances in syngas production include plasma pyrolysis which has been applied to the production of syngas from biomass. Pyrolysis is the thermochemical decomposition of organic material at elevated temperatures without the participation of oxygen. Plasma pyrolysis applied to syngas production is the breakdown of hydrocarbon molecular bonds into a gaseous form using plasma torches.

A number of patents have been issued since then for what is now known as steam reforming of natural gas. Among these patents is U.S. Pat. No. 6,706,770 issued to Air Products and Chemicals for a process for the simultaneous production of methanol and hydrogen synthesis gas including some of the intermediate products together with recycling of synthesis gas. Modern methanol production has been made more efficient through use of catalysts capable of operating at lower pressures, the modern low pressure methanol (LPM) was developed by Imperial Chemical Industries, Ltd. (ICI) in the late 1960s with the technology now owned by its acquirer-in-interest (Johnson Matthey), which is a leading global licensor of methanol technology.

Currently, the most widely used catalyst is a mixture of copper, zinc oxide, and alumina first used by ICI in 1966. At 5-10 MPa (50-100 atm) and 482° F. (250° C.), in a re-iterative process it can catalyze the production of methanol from carbon monoxide (CO) and hydrogen ($H_2$) with high selectivity (>99.8%):

$$CO + 2H_2 + \text{Catalyst} \rightarrow CH_3OH$$

Today, synthesis gas is most commonly produced from the methane component in natural gas, because natural gas contains hydrogen. Three processes are commercially practiced. At moderate pressures of 4 MPa (40 atm) and high temperature of approximately 1,562° F. (850° C.), methane reacts with steam on a nickel catalyst to produce syngas according to the chemical equation:

$$CH_4 + H_2O \text{ Steam} + \text{Catalyst} \rightarrow CO + 3H_2$$

This reaction, commonly called steam-methane reforming, is endothermic, and the heat transfer Limitations place limits on the size of and pressure in the catalytic reactors used. Methane can also undergo partial oxidation with molecular oxygen to produce syngas, as the following equation shows:

$$2CH_4 + O_2 \rightarrow 2CO + 4H_2$$

This reaction is exothermic, and the heat given off can be used in-situ to drive the steam-methane reforming reaction. From an analytical view, this equation can be expressed as the following: $CH_4 + 1.5O_2 \rightarrow CO + 2H_2O$ and can be seen as a very exothermic reaction in providing thermal input to the previous steam-assisted equation. When the two processes are combined, it is referred to as autothermal reforming. The high pressures and high temperatures needed for steam-reforming require a greater capital investment in equipment than is needed for a simple partial-oxidation process; however, the energy-efficiency of steam-reforming is higher than for partial-oxidation, unless the waste-heat from partial-oxidation is used.

It is to be observed that the production of synthesis gas from methane and steam produces three moles of hydrogen gas for every mole of carbon monoxide, while the methanol synthesis consumes only two moles of hydrogen gas per mole of carbon monoxide. One way of dealing with the excess hydrogen is to inject carbon dioxide into the methanol synthesis reactor, where it, too, reacts to form methanol according to the equation:

$$CO_2+3H_2 \rightarrow CH_3OH+H_2O$$

In 2010 U.S. Pat. No. 7,842,264 to Cooper, Tang et al. was issued. This patent relates to a process and apparatus for removing particulate, metals, sulfur dioxide, NOx and carbon dioxide, sequentially, from a gas stream using a series of reactors employing a "supersonic nozzle" (i.e., injecting at a range of designed Mach speeds) and a subsonic nozzle to break up an injected liquid stream into very small high speed liquid droplets which react, capture, encapsulate and then remove the pollutants. A supersonic nozzle is described as a de Laval convergent-divergent nozzle and is well-known to those skilled in the art. The pollutant-containing droplets are then "grown" to such size that they easily may be separated and removed from the swiftly-moving gas stream by means of an aerodynamic coalescer for separating the liquid phase from the gas phase. That patent also discloses that the recovered $CO_2$ may be passed through a known shift reactor to produce CO and then through a known methanol synthesis process to produce methanol using conventional principles of thermo-chemistry. In like manner, that patent discloses the production of ethylene, ethanol, ethylene dichloride, and polyvinylchloride (PVC) from such recovered $CO_2$ using conventional principles of thermo-chemistry.

Molecular Surface Chemistry

Molecular surface chemistry describes the phenomena that occur at the surfaces or interfaces between one molecule with another molecule. It deals with molecular surface energy transfer, electron charge transfer, adsorption, dissolution of original bonds, reformation of new bonds, intermediates and transitional dissociation and re-association of possible new bonding or pairing of components, desorption, mass and energy transfer, catalysis, and so forth. Since the formation of a new surface involving reactants requires breaking of attractions between the original constituent molecules, which is an endothermic process, the surfaces of the involved molecules are made relatively more unstable and involve the flow of positive free energy of formation. Surfaces contribute such free energy to the total system, which is also known as surface tension. Nevertheless, in an energy conservation mode, the system tries to minimize such unfavorable free energy at the involved surfaces. Such a surface quickly makes attraction with other molecules available to the system. The result is to reduce surface tension. The Oxford University Physical and Theoretical Chemistry Laboratory provides lectures and written explanation of such molecular surface chemistry as described by the Applicant. The U.S. Department of Energy's Brookhaven National Laboratory (BNL) provides a very descriptive pictorial illustration of such molecular surface chemistry, as shown in FIG. 1.

Surface Chemical Dynamics are described by BNL's Chemistry Department thusly: "A molecule's perspective on surface chemistry—[FIG. 1] schematically depicts, at the molecular level, the richness of the phenomena involved in the transformation of reactants to products at the surface of a material. A molecule may scatter off the surface, experiencing no or some finite degree of energy exchange with the surface. Alternatively, molecule-surface energy transfer can lead to accommodation and physical adsorption or chemical adsorption. In some cases, physisorption is a precursor to chemisorption, and in some cases, bond dissociation is required for chemisorption. Charge transfer plays a critical role in some adsorption processes. Once on the surface, the adsorbed intermediate may diffuse laterally with a temperature dependent rate, sampling surface features including adatoms, vacancies and steps. They may become tightly bound to a defect site. Various adsorbed intermediates may meet, either at defect sites or at regular lattice sites, and form short-lived transition state structures and ultimately product molecules. Finally, products desorb from the surface with a temperature dependent rate, imparting some fraction of the energy of the association reaction to the surface. The goal of surface chemical dynamics is to identify the roles, quantify the rates and understand the physics of these various mechanistic steps that comprise the surface chemical transformation."

It is important to note that in previous implementations during the past fifty years of the study of molecular surface chemistry, almost every documented instance discussed used photon, photovoltaic, laser action, electro-chemistry, microwave, or ultrasound (as in sound-pulses to cause vibrations) to impart energy in trying to activate or measure chemical conversion or transformation. These documents mostly described the vibrational excitation of the molecules and their behaviors, and the results obtained in some form of conversion or transformation, and the issues of intended yield efficiency. Only silence exists for the previously "missing" energy transfer phenomenon called the supersonic shockwave.

The documents outlined above require a series of steps to provide very high energy input, including but not limited to, repeated heating and cooling as well as raising and lowering the pressure at several points in the process. In order to increase the efficiency of the process to produce methanol, any other hydrocarbon, or other organic and inorganic chemicals, it would be desirable to limit the required steps as well as to reduce the energy-input required in the overall process. Reduction in the number of steps would also reduce the CAPEX (capital expenditures) and the OPEX (operating expenses). The following is according to a MIT Paper dated May 11, 2009 called: "Thermodynamic Analysis of Coal to Synthetic Natural Gas Process" whose general conclusion is instructive and is universally applicable to a wide range of processes and applications in many other industries: The conventional thermodynamic comparisons between and among the major competing gasification technology providers: Lürgi, Siemens, KBR, ConocoPhillips, Shell, GE Energy/Texaco, and others always circled around comparing relatively minor variations or changes of energy-inputs, temperatures, pressures, use of catalysts and stoichiometric ratios resulting in the slightest incremental yield-rate improvements but all within the range of 55% to 62%, and a 65% yield-rate becomes an ideal goal. Very little novel thinking and breakthrough has been introduced. To reach anywhere over a 70% yield-rate, extraordinary high consumption of energy and pressure inputs are required thus making it a costly sacrifice and uncompetitive with the others.

SUMMARY

The present disclosure relates generally to a method and apparatus for directly producing methanol, other alcohols and hydrocarbons, and other organic and inorganic chemicals, through the use of a supersonic shockwave reaction mechanism, which is intended to reduce the CAPEX and OPEX of the users because of its energy, time and cost efficiencies. The supersonic shockwave (as the physical collision-impact) itself is the energy and mass transfer phenomenon and it can function as a catalyst itself. The impact of the shock-collision with any reactant serves as an "impact-surface" to enable surface chemistry for the reactant.

In particular, in this disclosure collision physics, by means of the supersonic shockwave reaction and interaction mechanism, forms the proper and necessary reaction mechanism for energy-and-mass transfer into molecular surface chemistry. It will be understood as collision physics inducing collision chemistry at the molecular surfaces. The intended chemical products are reacted and formed when the proper balance of reactant chemicals are injected in stoichiometric molarity ratios matching the desired reactions to form products as predicted in balanced equations. The conversion or transformation reaction will occur in a split-second in a localized reaction zone. The energy required will be initially very endothermic delivered by the energy of the shockwave and shock collision/interaction at the point-of-impact (exactly where the energy is needed for activating the reaction), and then followed by another phenomenon of rapid cooling and pressure drop (which physicists describe as the "Joule-Thomson (Kelvin) Effect") underneath the "stern" of the shockwave as the reactants pass beyond the shockwave.

The term "Joule-Thomson (Kelvin) Effect" as used in physics and thermodynamics describes the temperature change of a gas or liquid when it is forced through an opening, such as an open-valve (nozzle) or a porous plug while no heat is exchanged with the environment. This phenomenon can occur either in a vacuum or in atmospheric environment. As a gas expands, the average distance between molecules grows. The expansion causes an increase in the potential energy of the gas. Since the present method and apparatus are designed so that no new work is done or extracted in this expansion process and no heat is transferred, the total energy of the gas remains the same because of the conservation of energy. The increase in potential energy implies and signifies a decrease in kinetic energy, and therefore a decrease in temperature. The rapid cooling and pressure drop as the reactants pass beyond the shockwave enables "locking-in" the reactions-converted state of the end-product of the collision chemistry reaction in a very exothermic mode, with no possibility of reaction-reversal because there will be no equilibrium state for the reaction just concluded. Such free expansion of the gas causes a rapid decrease in temperature. As molecules move away from each other, pressure also decreases. This adiabatic (no heat exchanged) cooling is an irreversible process. This rapid cooling with associated rapid temperature and pressure drop is achieved without another artificial or mechanical input of energy to cause the cooling, and thus is a great savings in energy-and-cost efficiency. And a moment later, the associated temperature and pressure will begin to recover to nearer ambient, but still slightly sub-atmospheric.

As understood by those in the practice, Hess's Law is observed as follows where $\Delta H^\ominus$ is the standard energy of the reaction and $\Delta H_f^\ominus$ is the standard energy of formation.

$$\Delta H^\ominus_{reaction} = \Sigma \Delta H^\ominus_{f(product)} - \Sigma \Delta H^\ominus_{f(reactants)}$$

Application of Hess's law to the current invention explains the locking-in the state of the end-product: At the collision-impact of the shockwave(s), all molecules in reactant gases are affected by the shockwave and discontinuities therein, and there can be no escape from its effect. Hess's Law explains that energy or enthalpy change ($\Delta H$ values) for any chemical or physical process is independent of the pathway or number of steps required to complete the process. Only the initial and final states are important as expressed in the final result.

The term "enthalpy" ($\Delta H$) is a preferred expression of system energy changes in many physical chemistry and physics measurements, because it simplifies certain descriptions of energy transfer. Enthalpy change accounts for energy transferred to the environment at pressure through expansion or through heating. Since total enthalpy, H, of a system cannot be measured directly: therefore the change in enthalpy, $\Delta H$, is a more useful quantity than its absolute value. The change ($\Delta H$) is positive in endothermic reactions, and negative in heat-releasing exothermic processes. The $\Delta H$ of a system is equal to the sum of non-mechanical work done on it and the heat supplied to it. Enthalpy ($\Delta H$) is a preferred way to describe the energy change status of the Shockwave Reaction Mechanism ("SRM"), instead of Gibbs Free Energy, because the SRM is not related to nor dependent on the Temperature$_{(Kelvin)}$ of the environment under Gibbs. Since Gibbs Free Energy is the maximum amount of non-expansion work that can be extracted from a closed system, this maximum can be attained only in a completely reversible process. When a system changes from a well-defined initial state to a well-defined final state, the Gibbs Free Energy ($\Delta G$) equals the work exchanged by the system with its surroundings, minus the work of the pressure forces, during a "reversible" transformation of the system from the same initial state to the same final state. In the present case, the SRM does not represent such a closed system with reversible reactions. The SRM is collision-physics that could occur regardless of what the environment may be at any temperature and/or pressure, any changing temperature and/or pressure, at any time and even while in process. It applies universally in collisions of galaxies, stars, planets, molecules and atoms. And SRM's collision-physics causes collision-chemistry. Therefore, the Gibbs system does not describe the SRM, and should not be used as a measuring yardstick.

When the proper balance of reactant chemicals is injected in stoichiometric molarity ratios matching the desired stable final products as predicted in balanced equations, it will produce such results by applying Hess's Law. All reaction-intermediates are transitional and will rapidly reform or recombine into the end-product that possesses the lowest state of energy when all intermediates and transitional reactions are "netted out" in the rapid exothermic condition that results in a stable end-product at much lower range of temperatures—closer to operational standard. It is well-known that if the net enthalpy change is negative ($\Delta H^\ominus < 0$), net the reaction will be exothermic and is more likely to be "spontaneous" (which means: in "a split-second"). Such exothermic reactions release heat to the gas phase while the end-product will be cooler and remains "locked-in" inside a lower state of energy. That lower state and stability effect helps with predictability of results and product-selectivity. The rapid cooling Joule-Thomson (Kelvin) Effect prevents any possibility of reversibility of an equilibrium situation. For any irreversible process, the entropy will increase. Hence removal of heat from the system (cooling) is necessary and is intended to maintain a constant internal entropy for an irreversible process in order to make it isentropic. This is most important and apparent because in the SRM, the design of the aerodynamic tubing structure (such as the open end nozzle 13 in FIG. 3) incorporates an open-end nozzle to where the reactants that have formed the product are forced to move and exit, and where "free-jet expansion" of the product-molecules inter alia is intended and allowed upon the exit. That enables the rapid cooling of the reactants that have just formed the product, making the irreversible condition occur.

Additionally, the selectivity among resulting compounds of the same family of the same chemical components can be further defined with similar net enthalpy values. For such discrete product-selectivity, the application of catalyst expertise is desired. Otherwise, Hess's Law is allowed to maximize the production-effect and product-selectivity, where the resulting product possessing the lowest state of enthalpy of formation and the most stability will predominate. FIG. 11 shows a computer-enhanced image of Schlieren Photography of "free-jet" expansion of gases exiting an open-nozzle (i.e., the visualization of the Joule-Thomson (Kelvin) Effect.) As shown, this visual image also conveys the realization that distance and time (at a moment later) away from the exit of the nozzle will moderate and dissipate the shockwave effect.

It is also important to understand that the current method of conventional thermodynamic input of high pressure and high temperature into any potential chemical reaction system may be inadequate to actually cause the activation of reactions until the pressure and temperature are so overwhelming that the vibrational energies of the molecules cause them to "bump" into each other unavoidably, vigorously and reactively. That is the current basis for conventional thermo-chemistry's usage of high pressure and high energy (far in excess of that which are adequate and sufficient to cause the desired reactions), for which the present method and apparatus is intended to provide an alternative solution.

As a natural illustration: In deep underground Natural Gas formations, the $CH_4$, $CO_2$ and $H_2$ have co-existed and have not reacted for many millions of years under High Pressure High Temperature (HPHT) conditions of 400° to 1,500° F. and 200 psig to 1,500 psig. When tapped, together they shoot out from HPHT gas wells still unreacted with and among each other under such great pressure, because they travel in roughly near-parallel or concurrent paths. Some de minimis reactions may take place resulting from minor "bumping" as they shoot out of the deep well, but moving in a near linear flow does not provide sufficient collision physics for molecular surface chemistry to form products of reaction in any noteworthy quantity.

As another illustration: In many current Synthetic Methanation Processes, man-made operating conditions between 1,500 psig to 3,000 psig and over 1,750° F. are required to begin the reaction. Such extensive input of energy is intended to cause sufficient vibrational "bumping" among the reactants to drive chemical reactions. But these processes often reach equilibrium conditions with sufficient residence time allowing reversal of the reactions or producing undesirable side-reactions, ending in frustratingly low intended yields. Competing designer catalysts and re-iterative steps are required to maintain a greater yield to justify the energy spent.

Shockwave Reaction Mechanism:

The supersonic shockwave reaction mechanism (herein called "SRM" for short) is equally applicable to pre-combustion gas and to post-combustion gas, as its "target" for collision physics. Reactants are injected at Mach speeds via one or more supersonic nozzles to collide in a localized reaction zone with the "target(s)", which, inter alia, can be another gas, steam, vapor, or liquid reagent. Mach speeds may be achieved when a gas (or gases) is compressed by industrial gas compressor to a designed pressure above and beyond 100 psig and directed to exit a supersonic nozzle. For those skilled in the art, the designed Mach speeds can be easily and economically achieved, and such gas can be directed to exit a designed supersonic nozzle. The liquid reagent(s), acting as reactant(s) or target(s), are shattered into micro-droplets as they pass through the shock(s) (greatly increasing the surface area for interaction) contemporaneous to being exposed to temperature, pressure, and enthalpy discontinuities across the leading and trailing edge of the shock(s) in a localized reaction zone. Being the tiniest of droplets, they can be easily vaporized in the endothermic zone of the SRM.

The reactant(s) may be channeled into the localized reaction zone to collide with the target(s) at different angles to generate a variation of intensities of collision (varying energy, pressure and mass transfer parameters associated with the various angles of oblique shocks created by varying the input parameters of temperature, pressure and throughput of the supersonic nozzle) and the desired effects on product-formation. When accompanied by certain catalysts, different hydrocarbon chain structures and fuels can be formed. Moreover, two streams of the same reactants could be turned to collide upon the other stream to form a "designer longer-chain compound", such as Ethane colliding with Ethane to form Butane, and Butane colliding upon Butane to form Octane, and so on.

In the present method and apparatus, the supersonic SRM overcomes the reaction-barriers of pressure and energy constraints of conventional thermo-chemistry and thermodynamics to which the previously utilized reformed natural gas processes are subject. In the present method and apparatus, compressible fluids including reactants moving at supersonic speeds (Mach speeds) and their associated shockwaves (generated by such reactant gases as $CO_2$, $H_2$ and $CH_4$) are delivered to a common point within an injection tube where all molecules of the reactant gases must pass through the designed shockwaves creating a designed molecule-to-molecule collision. This is not coexistence and not just in a general turbulence region but in a localized shock-induced reaction zone. In general, Mach speeds in the range of Mach 3 to Mach 8 may be used or, preferably, Mach 4 to Mach 6. Within the injection tube, the shockwaves are regions where the pressure, temperature, enthalpy and entropy are changing rapidly and the colliding molecules are subject to Molecular Surface Chemistry, as described above. Due to the energy supplied by the shockwaves, the contacting molecular bonds are broken apart in endothermic reactions and then reformed in exothermic reactions to form a new product.

In this illustrative case, the energized reactants transform into product-methanol ($CH_3OH$) under the exothermic condition behind the shockwaves ("stern"), commonly described by laymen as "underneath the shockwave." This is a region of heat release accompanied by rapid drop of temperature and pressure. All molecules in the gas flow must pass through this region. No gaseous molecule could escape the shockwave effect in a designed-shaped tunnel. Physics governs. It is absolute. While the present method and apparatus does not exclude the practice of varying the temperatures and pressures within the injection tube, the conventional use of heat, pressure and other energy intensive inputs (as required in previous implementations) with their long "residence time" and energizing the vast spaces between the relevant reactant molecules are not required. However, it is desirable to maintain the temperature within the injection tube in the general area of the localized reaction zone in the range of 50° F. to 500° F., or preferably in the range of 300° F. to 400° F. This may be accomplished either by adding a "steam jacket" or employing an induction heating element surrounding the localized reaction zone of the injection tube.

It will be appreciated that increases in the temperature or pressure in the general area of the localized reaction zone will decrease the Mach speed collision-impact required to drive the chemical reactions. The use of steam as an energy source and motive force delivered via one or more supersonic nozzles may be beneficial on several counts: steam itself may be a reactant if a chemical reaction requires water; steam may deliver heat and energy to the localized reaction zone; steam may provide shockwaves in the localized reaction zone where it promotes molecular collisions and, as noted above, it reduces the Mach number required to generate the equivalent energy needed for the reaction. On the one hand, the previously described extra-energy inputs under conventional thermo-chemistry are largely the over-spent heating and pressurization of the entire equipment chamber and the non-related mass-matters, such as filling the relatively vast spaces and mass-matters in between the relevant participant molecules. In contrast, the present method and apparatus uses collision physics to cause collision chemistry directly at the point-of-use of energy, thereby at a fraction of the cost of conventional heat and pressure input and at a tiny fraction of the time involved.

"Collision physics" is the molecule-to-molecule contact or collision applied at the point-of-use, where the target and reactant are present interacting with the shockwaves which provide the input of kinetic energy, temperature and pressure, resulting in "near-instantaneous" reactions. The collision will cause the generation of heat and pressure at molecule-on-molecule contact. Energy and mass transfer is achieved in a "split-second"—breaking the original molecular bonds and causing new re-bonding and conversion into designer-products. The collision physics and surface chemistry reactions take place when the reactants are injected at supersonic speeds into a designed collision zone, i.e. the localized reaction zone, where each reactant is injected in various angles (ranging from almost concurrent angle, perpendicular 90° angle, near counter-current angle, and to fully counter-current angles) or the input conditions of each reactant are modified to generate oblique shocks of various angles to cause very high energy and pressure collisions in comprehensive reaction zonal coverage. The present method and apparatus uses high speed collisions, so all reactants are compressed and delivered at designed Mach speeds into collisions with each other. The physical shockwave causes collision-induced Molecular Surface Chemistry reactions, and such use is in sharp contrast to conventional thermo-chemistry. In essence, the energy-and-mass transfer occurs inside the SRM because of the effect of the shockwave(s). The reaction-products are heavily influenced by Hess's Law. When the proper balance of reactant chemicals in stoichiometric molarity ratios matching the desired stable final products as predicted in balanced equations is injected, the SRM should produce such results by applying Hess's Law. Additionally, with the aid of certain catalysts within the tubing (12 in FIG. 3), prior to the exit nozzle (13 in FIG. 3), the selectivity among resulting compounds of the same family having the same chemical components can be further defined. For such discrete product-selectivity, the application of catalyst expertise is desired. Otherwise, Hess's Law is allowed to maximize the production-effect and product-selectivity, where the resulting product possessing the lowest state of enthalpy of formation and the most stability will predominate.

To be simple and clear: SRM does not need to segregate each gas into its own separate stream. The gross inlet gas stream can be split into two or more streams, and one of said inlet gas streams (containing either of/or any combination of GHG: $H_2$, $CO$, $CO_2$, $H_2O$, $O_2$, $CH_4$) can be pressurized directly into the designed shockwave nozzle configurations to collide against the second or the third of the inlet gas streams of similar or different composition also re-vectored and entering from an opposing angle, or a designed angle, into the shockwave nozzle configurations to create the products under the SRM. The innovative concept is to use highly-pressurized gas components and collide them against one another at various designed Mach speeds—as long as the user has balanced out the requisite stoichiometric molarity ratios for each gas component in balanced equations, while using the SRM as the energy-and-mass transfer mechanism to create usable products. The chemical reaction results of Mach speed collisions will tend to narrow-down to those surviving the elimination of intermediates and having the lowest states of resulting enthalpy of formation, and sometimes the product-selectivity can be assisted by using special-purpose catalysts to shape the final selective outcome involving compounds of the same family. In addition to chemical reactants required for a particular product, steam may be jetted into the localized reaction zone at Mach speed to provide additional energy to support or to take part in the desired chemical reaction. In this sense steam functions as a compressible fluid reactant and is defined as such in the current disclosure.

To illustrate the collision energy occurring at the moment of impact, the following U.S. NASA (National Aeronautics and Space Administration) explanation is provided as shown in FIG. 12, NASA Graphic Table Illustration (Stagnation Temperature). In the first Graphic Table Illustration, NASA shows the Stagnation Temperature delivered at the collision-impact, which is described in the SRM of this invention as the "input of endothermic energy and pressure" into driving a collision-caused chemical reaction. NASA explains: For a moving flow of gas, there are several different values for the temperature of the gas. The "total temperature" is the sum of the static temperature and the dynamic temperature, and the value of total temperature depends on the Mach Number of the flow. If the moving flow is isentropically brought to a sudden halt on the body such as by a collision, NASA measures the "Stagnation Temperature". The stagnation temperature is defined as the temperature that occurs at a stagnation point (not-moving) on the object. Because the total overall temperature does not change through a shockwave, the stagnation temperature and the total temperature have the same value at a stagnation point. There exists a correlation between the temperature derived and the Mach speed of the flow. In the process of slowing or stopping the flow by collision-impact, the gas is heated due to the kinetic energy of flow. The amount of the heating depends on the specific heat capacity of the gas. If the specific heat capacity is a constant value, the gas is said to be "calorically perfect" and if the specific heat capacity changes, the gas is said to be "calorically imperfect". At subsonic and low supersonic Mach numbers, air is calorically perfect. But under low hypersonic conditions, air is calorically imperfect. Derived flow variables, like the speed of sound and the isentropic flow relations are slightly different for a calorically imperfect gas than the conditions predicted for a calorically perfect gas because some of the energy of the flow excites the vibrational modes of the diatomic molecules of nitrogen and oxygen in the air.

In FIG. 12, NASA has plotted the value of stagnation temperature in Fahrenheit for a standard day atmosphere as a function of altitude and Mach number. There are two sets of lines on the figure because of the inclusion of real gas effects. The solid line is the computed stagnation temperature for a calorically perfect gas and the dashed line is the computed stagnation temperature for a calorically imperfect gas. At the lower Mach numbers, below Mach 3, the values of stagnation temperature are the same, because the temperature is not high enough to excite the vibrational modes. But beginning around Mach 3, real gas effects become increasingly important with increasing Mach number.

For the perfect gas (as stated in NASA's equation), the stagnation temperature is derived from the isentropic total temperature equation:

$$T_t = T \times [1 + M^2 \times (\gamma-1)/2],$$

Where:
$T_t$=total temperature,
T=static temperature at a given altitude,
M=Mach number, and
γ=ratio of specific heats for a calorically perfect gas and has a constant value of 1.4 (for air).

For the calorically imperfect gas, the ratio of specific heats is not a constant but a function of the static temperature. Mathematical models for behavior of various gases have been developed.

FIG. 13 shows a graph related to the production of Methanol according to the formula:

$$CO_2 + CH_4 + 2H_2 + SRM \rightarrow 2CH_3OH$$

The left Y-axis shows the upstream edge temperature for the shockwaves for Mach numbers between M1 and M7 while the X-axis shows the corresponding downstream edge temperature of the shockwave. The line entitled "Cumulative Energy of Shocks—with Steam" shows the total energy of the reactants $CO_2$, $CH_4$, $H_2$, and steam. As shown in FIG. 13, if the upstream temperature (T1) is 250° F. and the Mach speed is approximately 6, the temperature at the downstream edge of the shock is approximately 3,700° F. It follows that at circa 3,700° F., the enthalpy at the downstream edge will be about 510 kJ/Mol with steam injection, and approximately 310 kJ/Mol without steam injection. As noted below, Methanol possesses an enthalpy of formation value of $\Delta H\,298_K = -238.4$ kj/mol. Thus, it is clear that Mach 6 shockwaves are generally more than sufficient for the SRM process and that Mach 4.3 (with Steam) or even Mach 5.8 (without Steam) shockwaves would be adequate.

It will be appreciated that for any desired product, the enthalpy of formation can be calculated based upon the enthalpy of formation of the reactants. The downstream shockwave temperature T2 of a specific gas with a specific heat capacity ratio, gamma (γ), and a Mach number M1 may be calculated as indicated below.

For Normal shocks:

$$\frac{T_2}{T_1} = \frac{2\gamma M_1^2 - \gamma + 1}{\frac{1}{2}(\gamma+1)^2} \times \frac{1 + \frac{1}{2}(\gamma-1)M_1^2}{M_1^2}$$

For Oblique shocks:

$$\frac{T_2}{T_1} = \frac{2\gamma M_1^2 \sin^2\theta - \gamma + 1}{\frac{1}{2}(\gamma+1)^2} \times \frac{1 + \frac{1}{2}(\gamma-1)M_1^2 \sin^2\theta}{M_1^2 \sin^2\theta}$$

The above formulas show that for normal shocks T2 is a linear function of T1 and, therefore, the Mach lines of FIG. 13 are straight lines. The enthalpy H of each reactant is calculated from the following formula:

$$H = C_p T$$

where Cp is that specific heat capacity at T2. This is also a linear equation. Assuming that each gaseous reactant is at about the same temperature in the localized reaction zone, the enthalpy of each reactant can be calculated. Cp is specific to each gas and, for the reactants in FIG. 13, is as follows:

$CO_2$=0.844 kJ/kg Deg. K [equiv. to 19.192 kJ/mole]

$CH_4$=2.220 kJ/kg Deg. K [equiv. to 138.75 kJ/mole]

$H_2$=14.32 kJ/kg Deg. K [equiv. to 7,160 kJ/mole]

Steam=2.260 kJ/kg Deg. K at 350 Deg. F (134 psia saturated)

[equiv. to 125.556 kJ/mole]

From the above table, it is apparent that Hydrogen is the principal source of energy due to its high heat capacity relative to the other reactants.

It is to be noted further that the temperature at the collision surface of a Mach-4 class or higher-Mach nozzle forming shockwave is well over 1,500° F. and sometimes ranging into 3,000° F., but at the underside of the Mach 4 or a higher-Mach shockwave is colder than −159.9° C. (and −255.95° F.), which would reflect the almost outer-space condition, ≤circa 80,000 to 100.000 feet above the earth. As an example of Temperature at the underside of a Mach 4-class shockwave, NASA provided a quick reference formula for shockwave caused by steam at 235 psig at nozzle entrance temperature of 855.57° Rankine and the temperature at the exit-underside of the shockwave is factored at 0.238496×855.57° Rankine=204.045° Rankine (or −255.95° F.). And as explained above, when the molecules move a little away from the shockwave effect a moment later in a partially-open system, with distance and time moderating and dissipating the shockwave effect, the associated temperature and pressure will begin to recover very quickly to nearer ambient condition, but still slightly sub-atmospheric. Therefore, in such a gas dynamic environment, having been formed by the endothermic reactions and moving-passing through the underside of the shockwave in an exothermic mode and out to an open recovery region, the cooled Methane and $CO_2$ cannot and will not survive as frozen but will take the state of near ambiency. Methane will rain-down as liquid and any available $H_2$ or $CO_2$ will regain in a gaseous state and flow onward.

DETAILED DESCRIPTION OF PREFERRED EMBODIMENTS

Figure 1:
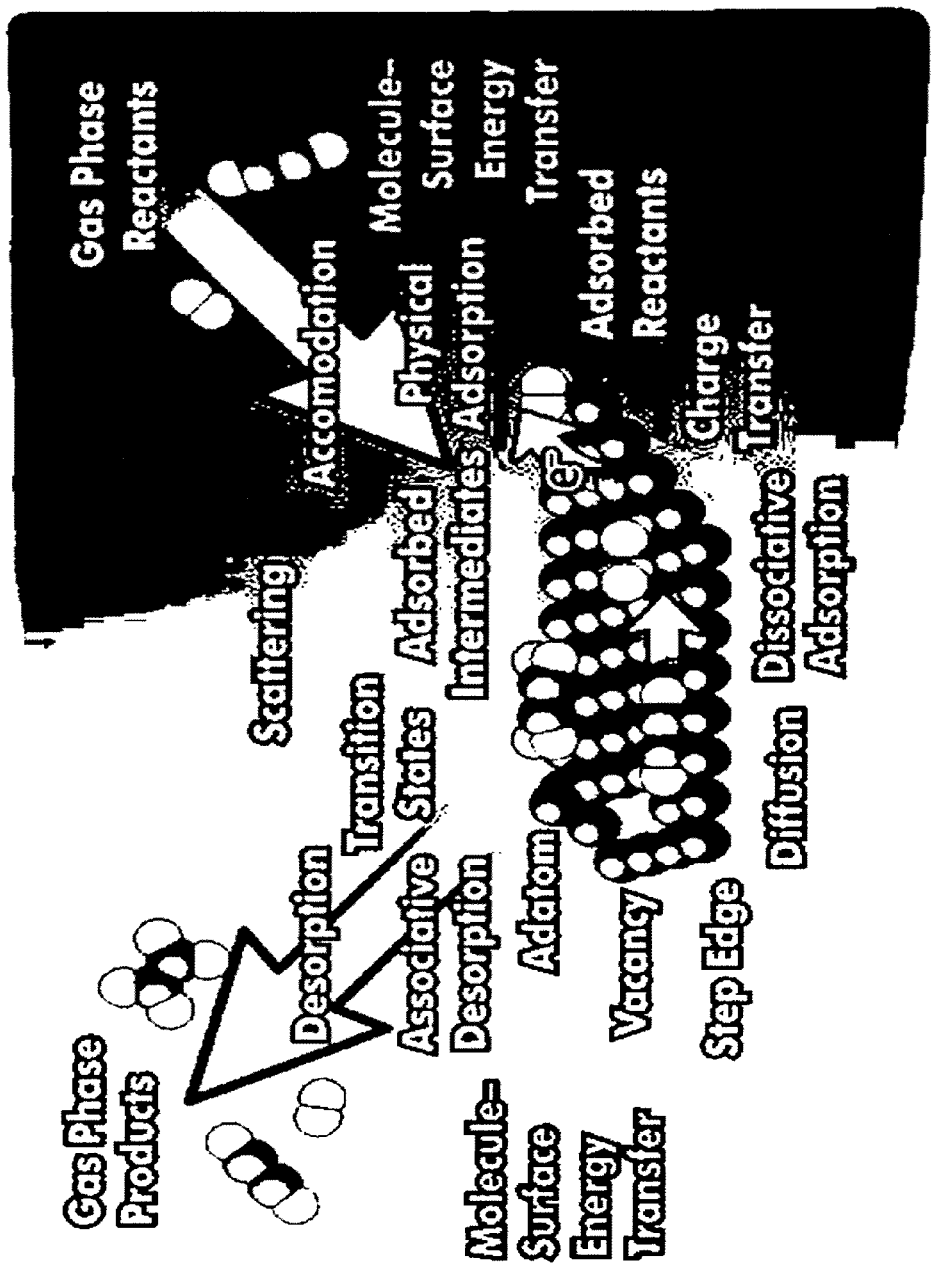
FIG. 1 shows a graphic illustration of molecular surface chemistry reactions provided by U.S. Department of Energy, Brookhaven National Laboratory.

In a preferred embodiment, hydrogen ($H_2$), methane ($CH_4$) and carbon dioxide ($CO_2$) are efficiently converted by the new SRM into low cost methanol ($CH_3OH$) or other carbon-related alcohols. The $CO_2$ may be derived from any biomass, organics, municipal solid waste (MSW), including producer gas (PG). The conversion of $CO_2$ or biomass into advanced fuels such as diesel, kerosene and gasoline is the essence of the "renewable" concept; the practical result of the new process is an alternative to the Fischer-Tropsch Process and its progeny. The SRM overcomes the reaction-barriers and energy constraints of the conventional thermo-chemistry and thermodynamics to which reformed natural gas processes previously implemented are subject. In accordance with the present method and apparatus, supersonic flows of compressible fluids (e.g., $CO_2$, $H_2$ and $CH_4$) and their associated shockwaves are delivered through one or more supersonic nozzles to a common region within a pressurized injection tube so that a multitude of collisions occur among the molecules of the several gases. The shockwaves are areas where the pressure, temperature, enthalpy and entropy are rapidly changing and this energy phenomenon is available at the points of collision within the shockwave regions among gas molecules to support the primary endothermic reactions. Then, as the products of reaction leave the front "bow" of the shockwave, they enter the "stern" of the shockwave and the second-in-sequence exothermic reactions occur to produce the desired end-product (e.g., methanol). The molecular collisions and consequent chemical reactions are called Molecular Surface Chemistry, because the interfacing surface of the molecules is large relative to the mass of the molecules. Consequently, the surface contact and reaction (such as the breaking of original bonding, converting and reforming of new bonding) is initiated and completed very rapidly. Since very many near-contemporaneous collisions within the SRM region occur, the total reaction process is completed nearly instantaneously.

The new process can be applied to any gas, including but not limited to CO, $CO_2$, synthesized gas, natural gas, producer gas or "syngas" to make "Carbon-Biogas-to-Liquid Fuel, or man-made Advanced Liquid Fuels" or other chemical compounds. Carbon-Biomass can be any form of carbon from any source, inclusive of common and uncommon sources with organic content, MSW, hydrocarbons such as bitumen, asphaltenes, pet coke, coal, any char, soot, and natural or synthetic gaseous or liquid forms thereof. If fuels or advanced fuels are utilized in stationary power or process heat generation, the process could re-convert them repetitively into renewable fuels in a "virtual near closed-loop recycling" of 99+% of the carbon emissions.

The energy, geometry, and type (normal or oblique) of the supersonic shockwaves is a function of the designated and applied Mach number for the supersonic jet and pressure, temperature and composition of the compressible fluid(s) delivered through the supersonic nozzle to the point-of-contact (shockwave collision). Similarly, the required energy of the shockwave collision (which is delivered by way of the designated Mach number) depends on the enthalpy of formation or the heat of reaction required to break the chemical bonds of the targeted chemicals so that an endothermic-then-exothermic reaction may help to convert the compound(s) and form a new product.

Figure 2:
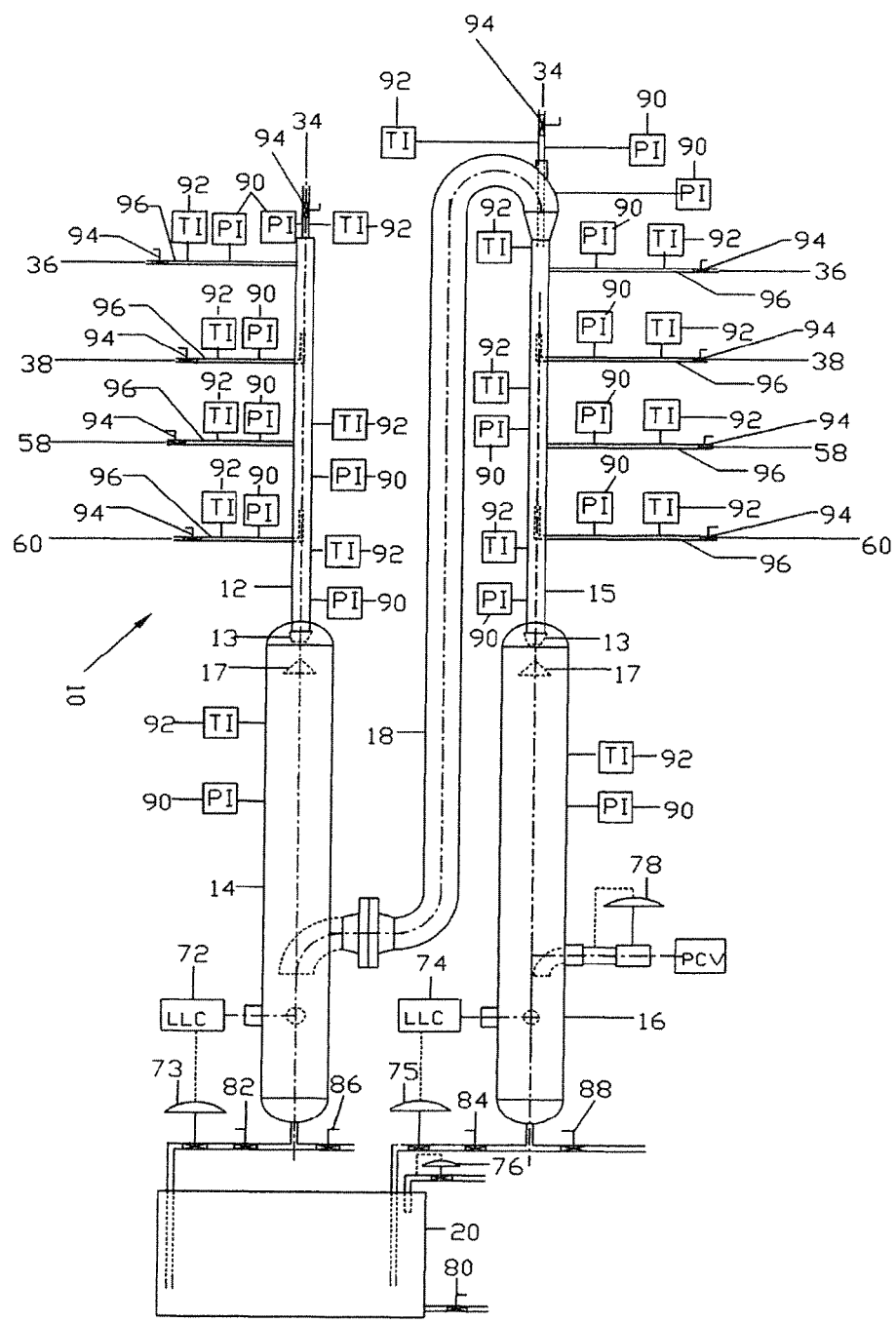
FIG. 2 shows a vertical view of an example of selected apparatus for producing methanol and other chemical compounds using the Shockwave Reaction Mechanism.
Figure 3:
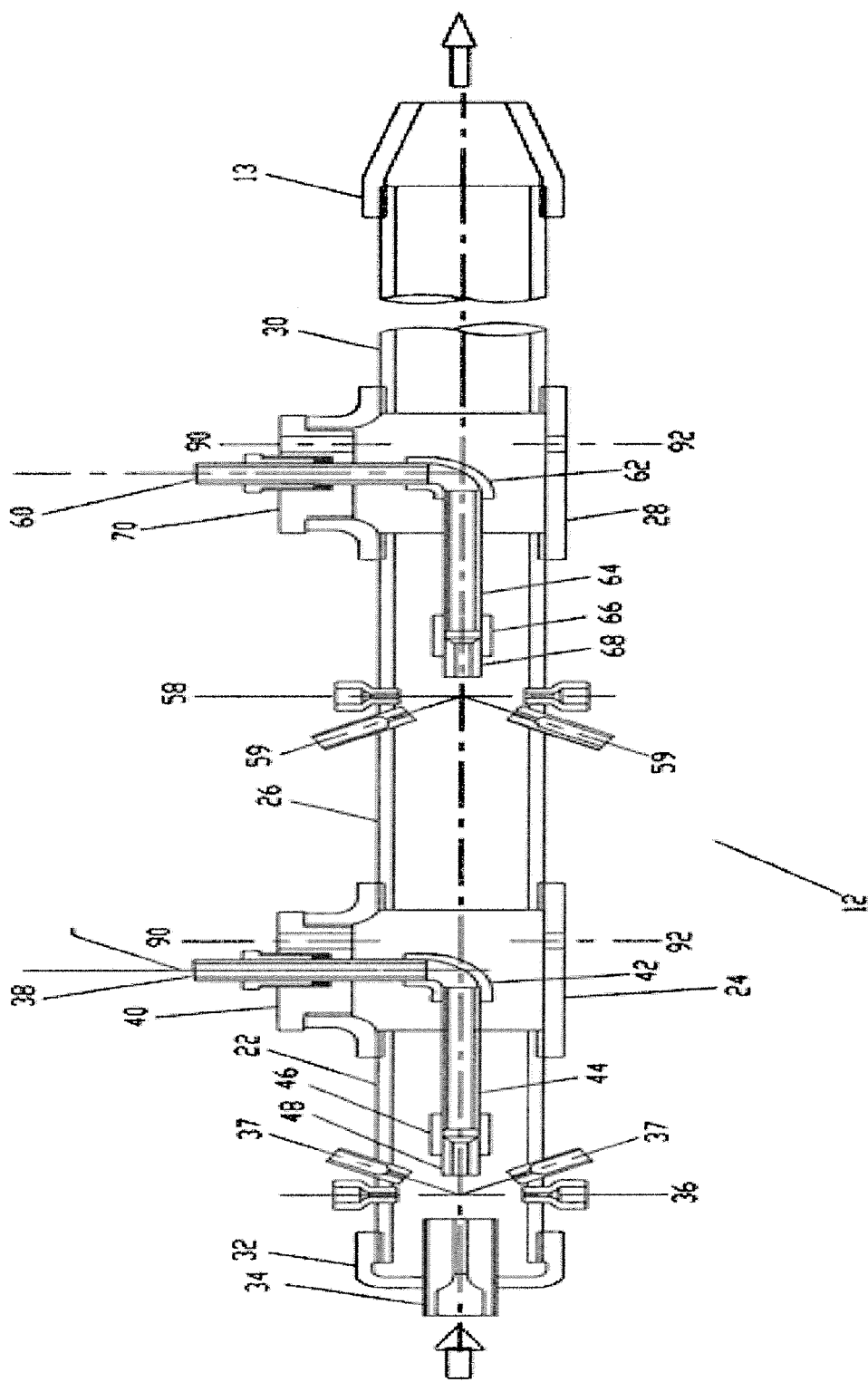
FIG. 3 shows a vertical cross-section of the injection tube for the apparatus of FIG. 2.

A preferred embodiment of the present apparatus is shown generally at 10 on FIG. 2 and comprises injection tubes 12, 15 shown in detail in FIG. 3, a first reactor 14, a second reactor 16, diffusers 17 located beyond the exit end of the injection tubes 12, 15, an interconnecting duct 18 and a product tank 20. The diffusers 17 provide additional spreading and mixing of the reactants (which may be gases, liquids or solids) to insure completion of the chemical reactions within the reactor.

Referring now to the injection tube 12 and FIG. 3, the injection tube comprises an upper stainless steel tubular section 22 which is affixed or threaded into an upper stainless steel Tee connector 24. A middle stainless steel tubular section 26 is affixed or threaded both into the upper Tee connector 24 and also into the lower stainless steel Tee connector 28. A lower stainless steel tubular section 30 is affixed or threaded into the lower stainless steel Tee connector 28. A plug 32 having a central aperture is affixed or threaded into the upper end of tubular section 22. A supersonic nozzle 34 is adjustably fitted in the central aperture of the plug 32 along the axis of the tubular section 22. A plurality of small supersonic nozzles 36 are adjustably threaded through the wall of the tubular section 22 so that their axes are perpendicular to the axis of the supersonic nozzle 34. Alternatively, the plurality of supersonic nozzles 37 may be placed at an angle to the axis of the nozzle 34 as shown in FIG. 3. Tube 38 is adjustably located in an aperture of the plug 40 which is affixed or threaded into Tee connector 24. The interior end of tube 38 is fastened to one end of the elbow 42 while tube 44 is fastened to the other end of the elbow 42. Connector 46 is adjustably fitted on the downstream end of tube 44 and supersonic nozzle 48 is adjustably affixed or threaded into the connector 46. As shown in FIG. 3, nozzles 34 and 48 are coaxial but 180 degrees opposed so that the supersonic jet flows from nozzles 34, 36, 37 and 48 are directed to a common region centered on the intersecting axes of all of the nozzles. It will be seen that all of the nozzles are axially adjustable to provide maximum efficiency of the apparatus. In addition, the pressure, temperature, flow rate, and gas type may be adjusted as may be desired.

A plurality of small supersonic nozzles 58 are adjustably affixed or threaded through the wall of the tubular section 26 so that their axes are perpendicular to the axis of the nozzle 68. A tube 60 is adjustably fitted through an aperture in plug 70 and connected at its interior end to one end of an elbow 62, the other end of which is connected to one end of tube 64, the other end of which is adjustably affixed or threaded into one end of connector 66. Supersonic nozzle 68 is adjustably connected to the other end of connector 66. Alternatively, the supersonic nozzles 59 may be placed at an angle to the common axes of nozzles 34 and 68. Nozzle 68 is coaxial with nozzles 34 and 48 and directed in the same direction as nozzle 48. As with the nozzles in the upper section, supersonic jet flows are directed to a common region, i.e., the localized reaction zone, centered on the intersecting axes of all of the nozzles. If desired, any of the supersonic nozzles 34, 36, 37, 48, 58, 59 and 68 may be two-fluid nozzles capable of delivering a finely divided liquid or solid carried by a compressible fluid jet. In FIG. 2, the nozzle 13 at the end of the injection tubes 12 and 15 may be a sonic or subsonic nozzle and is intended to provide cooling within the reactors 14 and 16 to compensate for the exothermic reactions in the localized reaction zone. It may be found desirable to feed injections to the nozzles 36, 37, 58, 59 in groups of one, two or three so that different quantities of gases or different gases and liquids may be injected into the apparatus without altering the basic design of the apparatus. This approach will enable the apparatus to produce many different products.

Liquid level controllers 72 and 74 control the level of the liquid product, e.g. methanol, in the lower ends of reactors 14 and 16 and direct excess product into the tank 20 through valves 73, 75. Liquid level controller 76 similarly controls the level of the product in the tank 20. Pressure control valve 78 controls the pressure in the second reactor 16, and therefore influences the pressure in the first (upstream) reactor 14, at the point where the gaseous products leave the apparatus 10. Valve 80 located near the bottom of tank 20 permits withdrawal of product from the product tank 20. Shut-off valves 82, 84 and drain valves 86, 88 are provided, respectively, for the reactors 14 and 16. In some cases, it may not be necessary to use the lower portion of injection tubes 12, 15 or the secondary reactor 16 and, in this event, these parts of the apparatus may be turned off. Pressure indicators 90 and temperature indicators 92 are located, respectively, in the upper and lower Tees 24 and 28 to measure the pressure and temperature in the injection tubes 12 and 15 and in the reactors 14 and 16, respectively. Additionally, pressure indicators 90 and temperature indicators 92 are located at each injection point and within the reactors 14 and 16. Valves 94 are provided in the feed lines 96 to each injection point so that portions of the apparatus may be turned off, if desired.

If it is desired to produce methanol from the apparatus 10, carbon dioxide may be provided, for example, to the nozzles 34 for both reactors 14 and 16 and methane may be, for example, provided to nozzles 48 and 68 for both reactors 14 and 16. Hydrogen may be provided, for example, by the sets of nozzles 36, 37 and 58, 59 for both reactors. Within the reactor the following reactions occur for the methanol example, together with the final materially balanced equation shown in Eq. 5 (below), as in FIG. 4A:

 1.

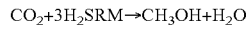 2.

 3.

 4.

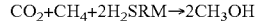 5.

The methanol and water, if any, will drop to the bottom of the reactors and enter the tank 20 through valves 73 and 75 operated by liquid level controllers 72 and 74 while any unreacted gases will leave through the pressure control valve 78. If the gaseous supplies are properly balanced, only methanol should be produced and enter the tank 20. If there is an imbalance of gas inputs, then there is a possibility of CO and $H_2$ appearing in the exit stream via valve 78 and these may be used directly as a fuel, or re-directed into a secondary reactor to complete their consumption in a secondary methanol production.

When any liquid chemical reagent is injected into the shockwave region of the reaction mechanism, even the tiniest droplets exiting from the best of the commercially available spray nozzles (which are usually in the range of 50 microns to 200 microns) will be shattered by the shockwave into much tinier micro-droplets approaching the micronic sizes. This will multiply the surface area of the reagent liquid to meet and inter-mix with the targeted reactant for much faster and more intimate inter-mixing on a near-molecular level thus producing near-instantaneous chemical reaction and compound conversion. This is a clear example of "molecular surface chemistry" because the fine droplets have a large "ratio of surface area to mass" which makes it possible for the rapid mass transfer chemical reactions to take place and serves to simplify the chemistry as well as to significantly reduce overall capital and operating costs.

Employing predictable designed mid-range reaction temperatures (equivalent to designing between 275° F. and 675° F.), "collision physics" with a catalytic combination (such as Iron and Zeolite, and other modern catalysts) could limit the reformation of longer carbon-chains ranging from a $C_7$ to $C_{10}$ (leading to formation of benzene-like, gasoline-like and kerosene-like liquids).

Using mid-range Mach Speeds (between 2,000 ft./sec. to 6,000 ft./sec.), a stream of Reactant Gas (such as $H_2$) as small as at approximately 10% in Mass (weight) relative to the 90% Mass of the Targeted Gases/Vapors or Liquids, could be accelerated to collide and cause the generation of heat and pressure at the molecule-on-molecule collision—energy and mass transfer in a "split-second"—breaking of original molecular bonds and causing new re-bonding and conversion into designer-products. It is observed that a gas, such as hydrogen gas ($H_2$), can be accelerated to very high speed when assisted by a mild heating, such as via an electrical heater or other heating means, in conjunction with compression into a range of Mach speeds. $H_2$ gas is the lightest, and more easily and economically heated reactant gas. In a situation when two opposing reactant candidates are $CO_2$ (at the main flow) and $CH_4$ (at the counter-flow), $H_2$ is recommended to be injected at 90° angle to their flows, or at some counter-current angle to its major target reactant, to achieve the better collision effect. The follow-on, continuing and repetitive collisions and after-collisions down the course will help to complete the necessary intimate contact among the reactants.

"Designer Application" Shockwave Reaction Mechanism ("SRM"):

Colliding any gas with another gas/vapor or liquid reagent at Supersonic Speeds provides the solution: colliding $CO+H_2$ or $CH_4+H_2$ with any combination of Carbon, CO or $CO_2$, $O_2$ with or without $H_2O$ (e.g., steam re-combination or re-forming) can form Alcohols, Polyethylene (PE) and Polypropylene (PP), and can add HCl or $Cl_2$ to form Ethylene Dichloride (EDC) or Dichloroethane (DCE) to make PVC Plastic, etc.

For the case of methanol production, the following reactions take place when the reactants are injected at supersonic speeds into a designed collision zone, where each reactant is injected in various angles (ranging from near concurrent angle, perpendicular 90° angle, near counter-current angle, and to fully counter-current angles) to cause very high energy and pressure collisions in comprehensive reaction zonal coverage. The equations are shown in near-contemporaneous time frame:

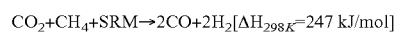

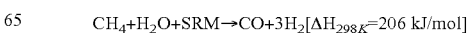

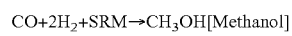

The final "netted out" materially balanced equation shows:

$$2CO_2 + 2CH_4 + 4H_2 + SRM \rightarrow 4CH_3OH \text{[Methanol]}$$

Figure 4A:
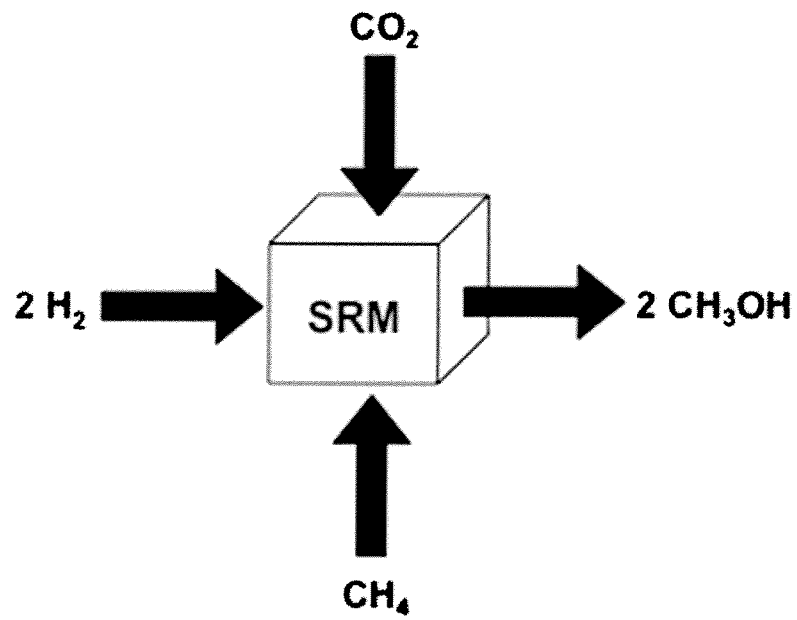
FIGS. 4A and 4B are block diagrams for a process in accordance with the present disclosure for the production of methanol.

Or, as shown in FIG. 4A:

$$CO_2 + CH_4 + 2H_2 + SRM \rightarrow 2CH_3OH \text{[Methanol 'A']}$$

Figure 4B:
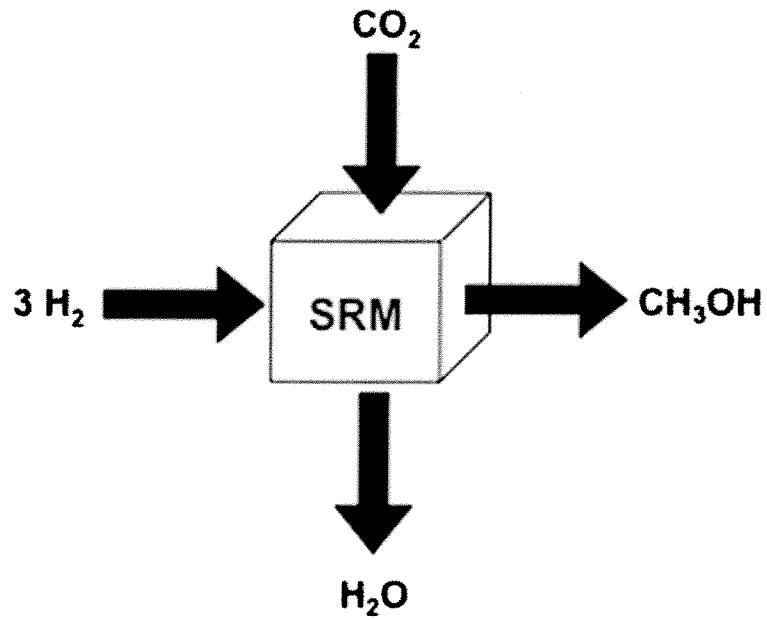

Sufficient residence time is engineered into the apparatus to allow the reformation of the desired compound. Methanol possesses the enthalpy of formation value of $\Delta H_{298K} = -238.4$ kJ/mol. The result showing a negative number is a stable alcohol product after the exothermic reaction. Alternatively, in the interest of making methanol from $CO_2$ without using $CH_4$ as shown above, there is another route that will make $CH_3OH$ and water $H_2O$ as shown in FIG. 4B:

$$CO_2 + 3H_2 SRM \rightarrow CH_3OH + H_2O \text{[Methanol 'B']}$$

This is wet methanol and the traditional way to separate the water from the methanol, among other ways, is to freeze water into ice, or to evaporate the one from the other. It will require a separate input of energy for that purpose.

Figure 5A:
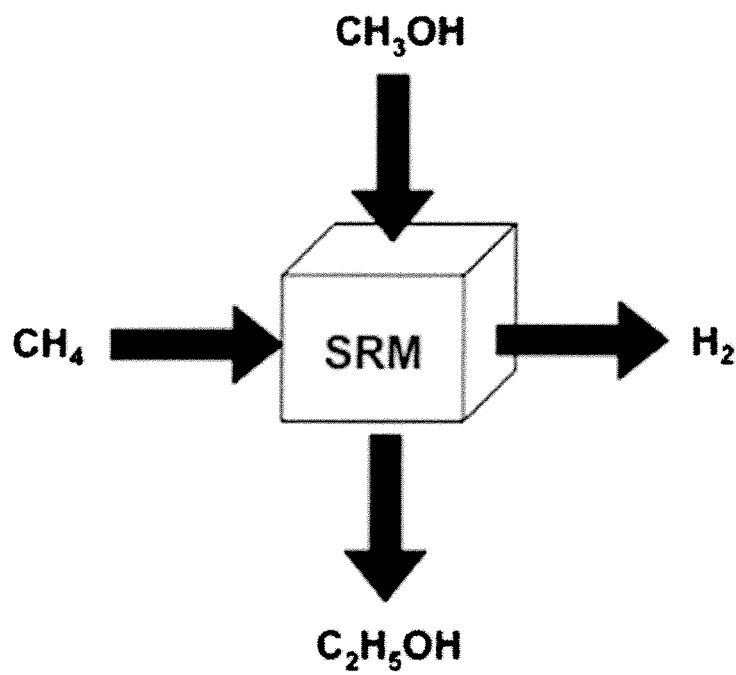
FIGS. 5A, 5B, and 5C are block diagrams for a process in accordance with the present disclosure for the production of ethanol.
Figure 5B:
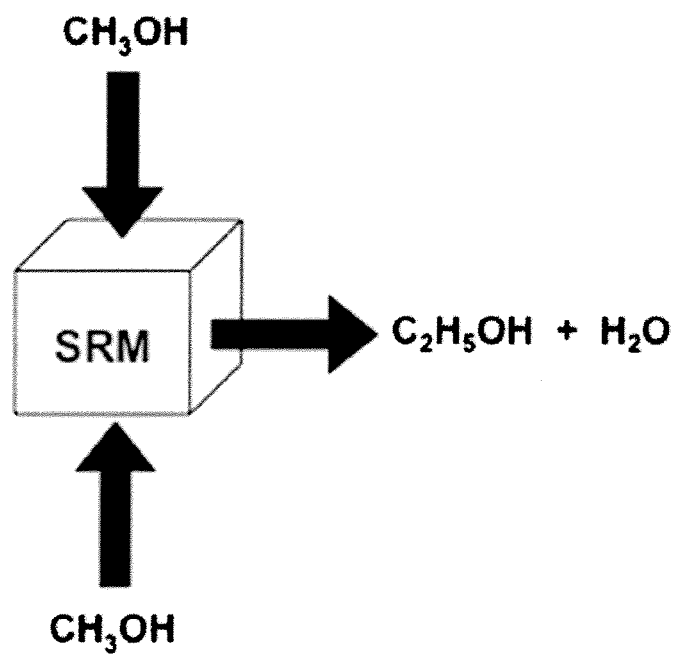

From the produced methanol (above), it is shown that the following ethanol product could be made as a stable alcohol product as in FIG. 5A and FIG. 5B:

$$CH_4 + CH_3OH + SRM/H_2 \rightarrow C_2H_5OH + H_2 \text{[Ethanol 'A']}$$

$$CH_3OH + CH_3OH + SRM/H_2 \rightarrow C_2H_5OH + H_2O \text{[Ethanol 'B']}$$

In the Ethanol 'A' application, the previously produced $CH_3OH$ (in the Methanol process immediately above) is used as feedstock. The Boiling Point of Methanol is very low at 64.7° C., 338 K, and 148° F. The reactant $CH_3OH$ is injected axially in the reaction tubular chamber via a two-fluid nozzle in which hydrogen gas ($H_2$) may serve as the carrier gas and catalyst, and the $CH_4$ gas also serving as feedstock is injected 180 degrees counter-axially as the second fluid-reactant in the injection tube at Mach speed. The $CH_3OH$ will be shocked and vaporized (or shattered into the tiniest micro-droplets and then vaporized) by the power of the supersonic jets thereby providing superior contact surfaces to enable the follow-on reaction. The desired collision reaction forming Ethanol 'A' will occur in such a hydrogen-rich reducing environment of the SRM.

In the Ethanol 'B' application, the previously produced $CH_3OH$ (as mentioned above) is used as the primary feedstock. Greater-than-half of the reactant $CH_3OH$ is injected axially in the injection tube via a two-fluid nozzle in which hydrogen gas ($H_2$) or steam shooting at Mach speed as the driving or motive force may serve as the carrier gas and catalyst. The less-than-half of the reactant $CH_3OH$ is injected 180 degrees counter-axially at Mach speed in which hydrogen gas ($H_2$) or steam may also serve as the carrier gas and catalyst. Some hydrogen gas ($H_2$) may also be injected at a Mach speed at a 90 degrees perpendicular angle to the axis into the zone where the two streams of $CH_3OH$ meet. Both streams of the $CH_3OH$ will be shocked and vaporized (or shattered into the tiniest micro-droplets and then vaporized) by the power of the supersonic jets thereby to enable the follow-on reaction. Then the $H_2$ gas (providing a reducing environment and serving as a catalytic participant) will help to break the formation of C=O and C—O bonds and to reform the new C—H and O—H bonds inside the SRM. The desired collision reaction forming Ethanol 'B' and water will occur in such a reducing environment of the SRM. Thus, the hydrogen gas ($H_2$) when injected at supersonic speed serves a reformative purpose.

Extensive collision shock (with its energy-and-mass transfer) delivered within a multiplicity of shockwaves and their after-effects thus enables chemical bond reforming, and produce the designed result. Sufficient residence time and opportunity for multiple follow-on collisions brought about by continuing shockwaves are engineered into the shaping and designing of the apparatus to allow Hess's Law to take effect by eliminating transitional and intermediate reactions thus leading to the reformation of the desired and more stable compounds. Those who are skilled in the art will employ aerospace and gas-dynamics principles to shape and design the apparatus to carry out the intended effects.

Figure 5C:
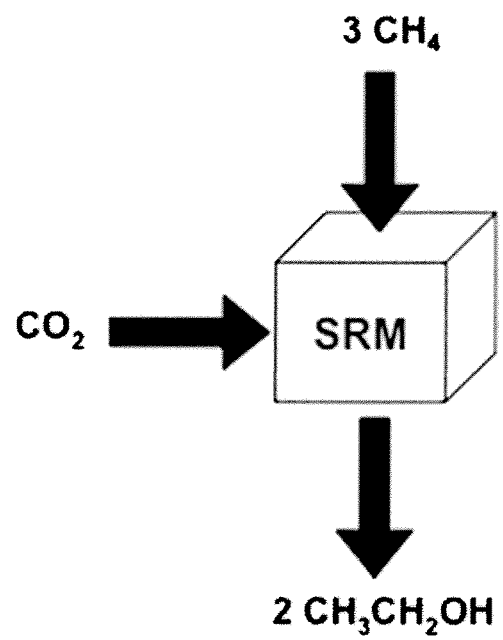

Moreover, in the interest of total overall conservation of resources, energy, and time in a total conservation mode, this invention (for example) could deploy the large supply of industrially captured $CO_2$ (see: U.S. Pat. No. 7,842,264) for additional duty as a higher value resource with overall sustainability and renewability characteristics to help make ethanol—leading to making ethylene and plastics. The final "netted out" materially balanced equation for making ethanol is shown in FIG. 5C:

$$CO_2 + 3CH_4 + SRM \rightarrow 2C_2H_5OH \text{[Ethanol 'C']}$$

The steps occurring physically, rapidly and contemporaneously are:

$$CO_2 + 3CH_4 + SRM \rightarrow 2C_2H_5O^* + 2H^* \text{(*radical caused by collision energy)}$$

$$2C_2H_5O^* + 2H^* + SRM \rightarrow 2CH_3CH_2OH \text{[Ethanol 'C']}$$

Ethanol possesses the enthalpy value of formation of $\Delta H_{298K} = -277.7$ kJ/mol. The result showing a negative number is a stable alcohol product after the exothermic reaction.

Ethylene is widely used in chemical industry, and its worldwide production (over 120 million tpy in 2010) exceeds that of any other organic compound. It is possible to make ethylene with this invention. From the methanol equations above, it follows that:

$$CO_2 + CH_4 + SRM \rightarrow 2CO + 2H_2 [\Delta H_{298K} = 247 \text{ kJ/mol}]$$

$$2CO + 2H_2 + 2H_2 + SRM \rightarrow CH_2{=}CH_2 + 2H_2O \text{[Ethylene—exothermic]}$$

A theoretical side-reaction or by-product, is as follows:

$$2CO + 2H_2 + 2H_2 + SRM \rightarrow CH_3{-}CH_3 + H_2O + 0.5O_2 \text{[Ethane+Water+}\tfrac{1}{2}O_2\text{]}$$

Figure 6:
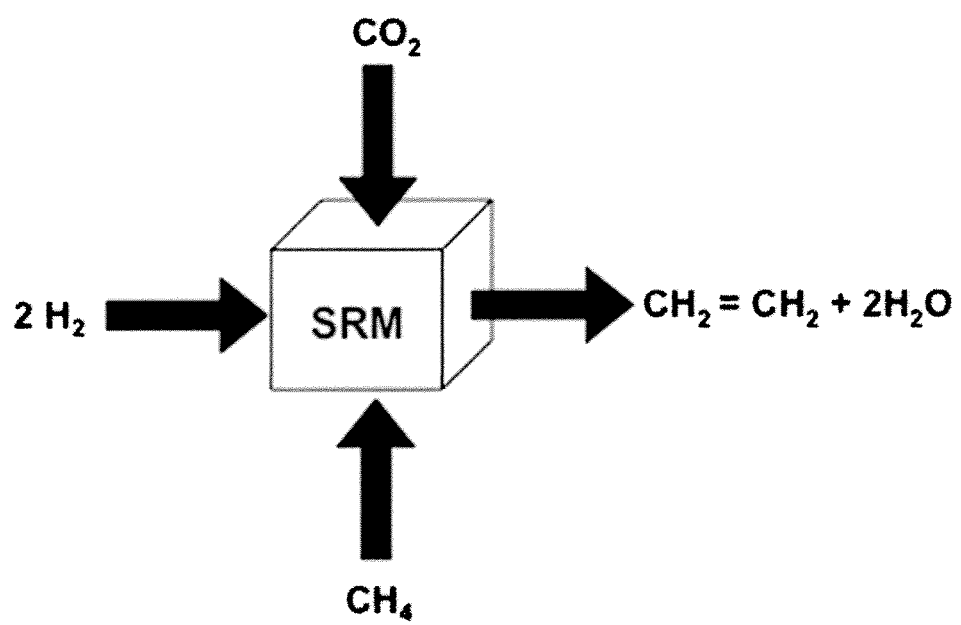
FIG. 6 is a block diagram for a process in accordance with the present disclosure for the production of ethylene.

However, under Hess's Law and in practical effect, by providing the second $+2H_2$ in the reactor, the result of making Ethylene and $2H_2O$ (exothermic) takes preference over making Ethane gas and $O_2$ gas due to the respective enthalpy states of all reactants in a rapidly falling temperature and pressure condition under the "stern" of the shockwave. The $O_2$ gas prefers competing for the available $2H_2$ and making the $2H_2O$ exothermically which will result in a more stable overall condition for all reactants, and the C=C bond of the Ethylene compound will not preferentially break to grab the otherwise available $H_2$ gas. The final "netted out" materially balanced equation is shown in FIG. 6:

$$CO_2 + CH_4 + 2H_2 SRM \rightarrow CH_2{=}CH_2 + 2H_2O \text{[Ethylene+water]}$$

By quickly removing the liquid water which is raining down to the bottom of a designed liquid-gas phase separation apparatus while the reactor chamber is still very warm, Ethylene [$\Delta H_{298K} = 52.4$ kJ/mol] [Boiling Point at −103.7° C. (−154.7° F.)] could be maintained as a separated gas product.

Figure 7:
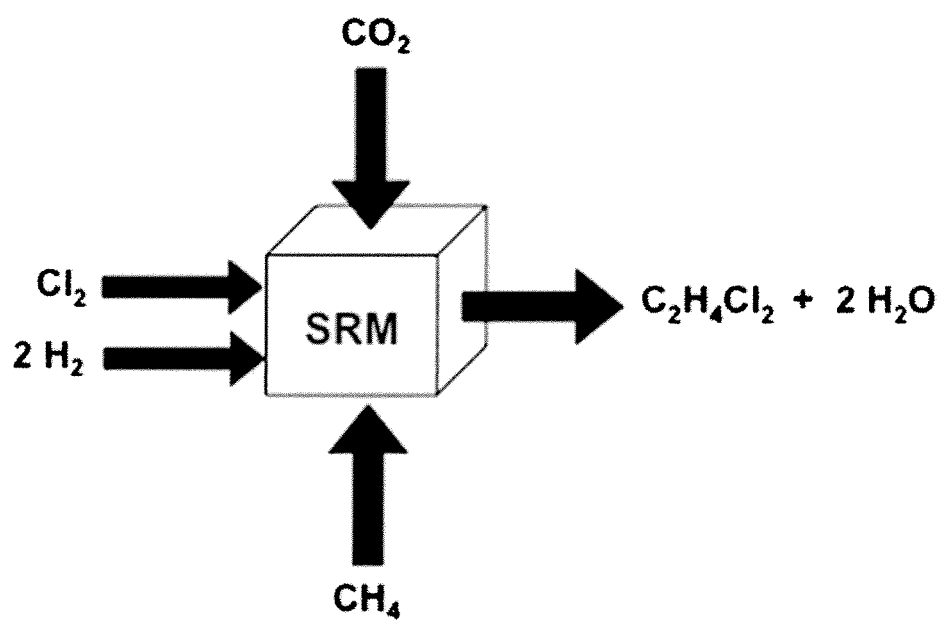
FIG. 7 is a block diagram for a process in accordance with the present disclosure for the production of dichloroethane.

To make plastics such as PVC, use the above Ethylene equation and add $Cl_2$ gas (or 2 HCl acid in correct proportioning with $H_2$ gas). The final "netted out" materially balanced equation is shown in FIG. 7:

$$CO_2+CH_4+2H_2+SRM \rightarrow C_2H_4Cl_2+2H_2O \text{[Dichloroethane—DCE]}$$

$$DCE_o+DCE_n+SRM \rightarrow \text{PVC Plastics}$$

Figure 8:
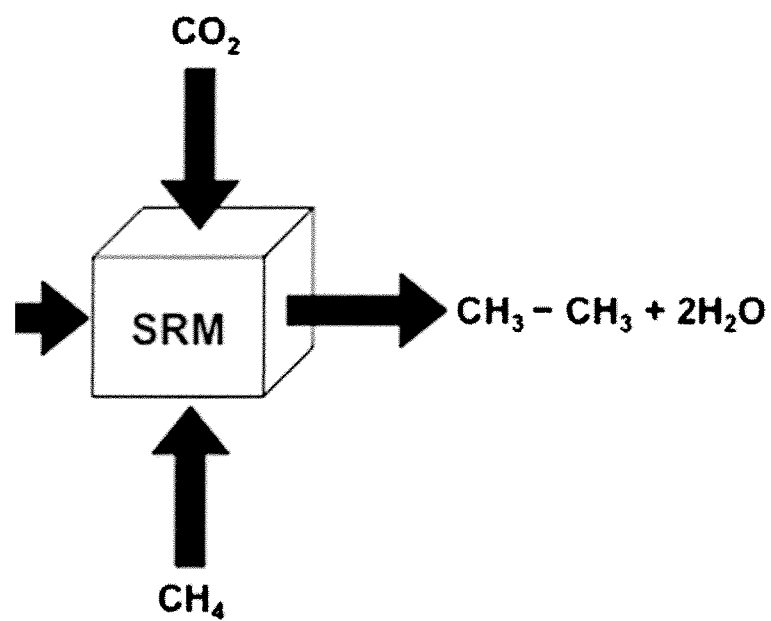
FIG. 8 is a block diagram for a process in accordance with the present disclosure for the production of ethane.

For making Ethane, add another $H_2$ into the previously described Ethylene equation as shown in FIG. 8:

$$CO_2+CH_4+3H_2+SRM \rightarrow CH_3CH_3+2H_2 \text{[Ethane]}$$

Figure 9A:
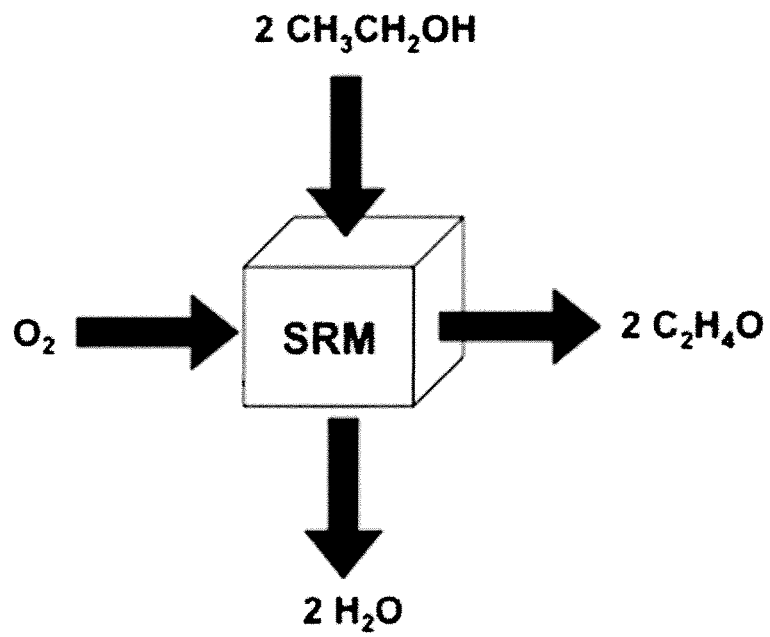
FIGS. 9A and 9B are block diagrams for a process in accordance with the present disclosure for the production of ethylene oxide.
Figure 9B:
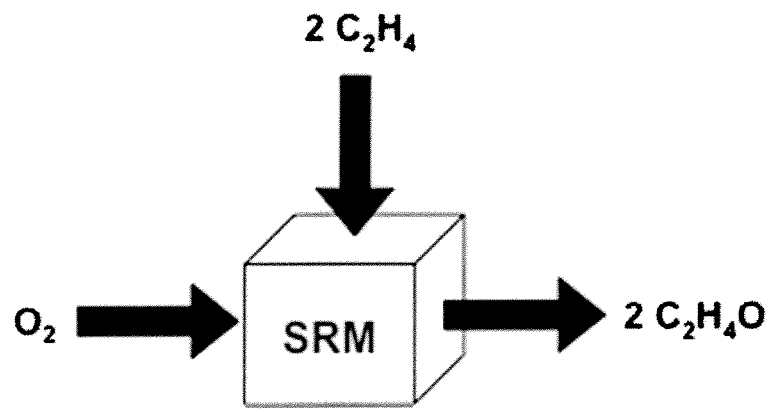

Ethylene Oxide ($C_2H_4O$) is an important chemical intermediate which has a current global consumption of over 30 million tpy. Most of $C_2H_4O$ is used to make Ethylene Glycol, but other major uses are for making ethanolamines, glycol ethers and various ethoxylates. $C_2H_4O$ is produced commercially in a vapor-phased reaction of Ethylene ($C_2H_4$) and Oxygen ($O_2$) over a silver-based catalyst. This reaction is exothermic and may involve unselective and competing side-reactions. Current thermo-chemical production methods require significant controls, and great effort to remove the heat from the system with conventional heat-exchange methods, but they still produce low yields. However, using the SRM of this invention, it is possible to make $C_2H_4O$ in at least two different ways commercially for higher yields in a shorter time in a catalyst-assisted reaction zone of the injection tube or the reactor chamber, such as using a silver-catalyst, as shown in FIG. 9A and FIG. 9B:

$$2CH_3CH_2OH+O_2+SRM \rightarrow 2C_2H_4O+2H_2O\text{[Ethanol Route][}\Delta H_{298K}=-52.6 \text{ kJ/mol]}$$

$$2C_2H_4+O_2+SRM \rightarrow 2C_2H_4O\text{[Ethylene Route]}$$

Ethylene Oxide possesses the enthalpy value of formation of $\Delta H_{298K}=-52.6$ kJ/mol. The result showing a negative number is a stable chemical-intermediate product after the exothermic reaction.

Figure 10:
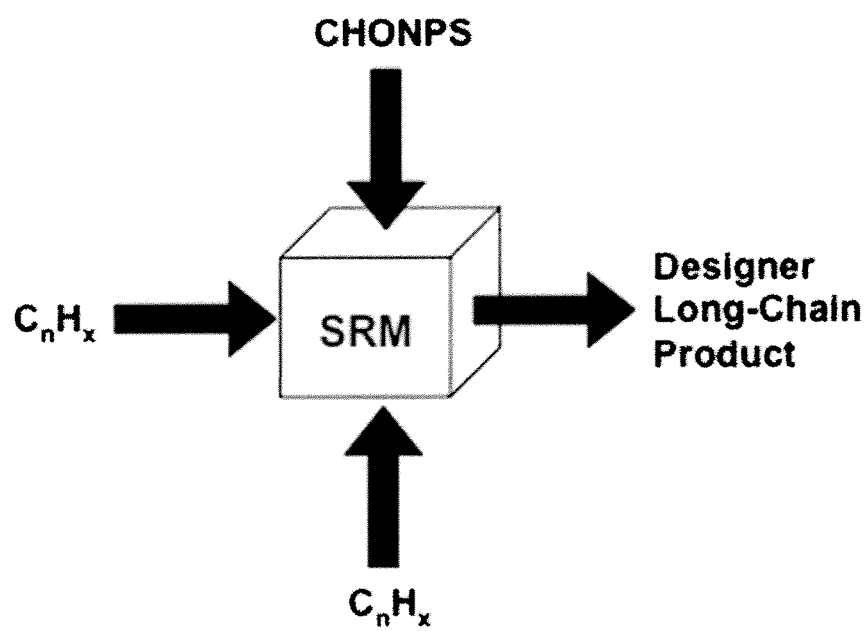
FIG. 10 is a block diagram for a process in accordance with the present disclosure for the production of any long-chain hydrocarbon or chemical compound.
Figure 11:
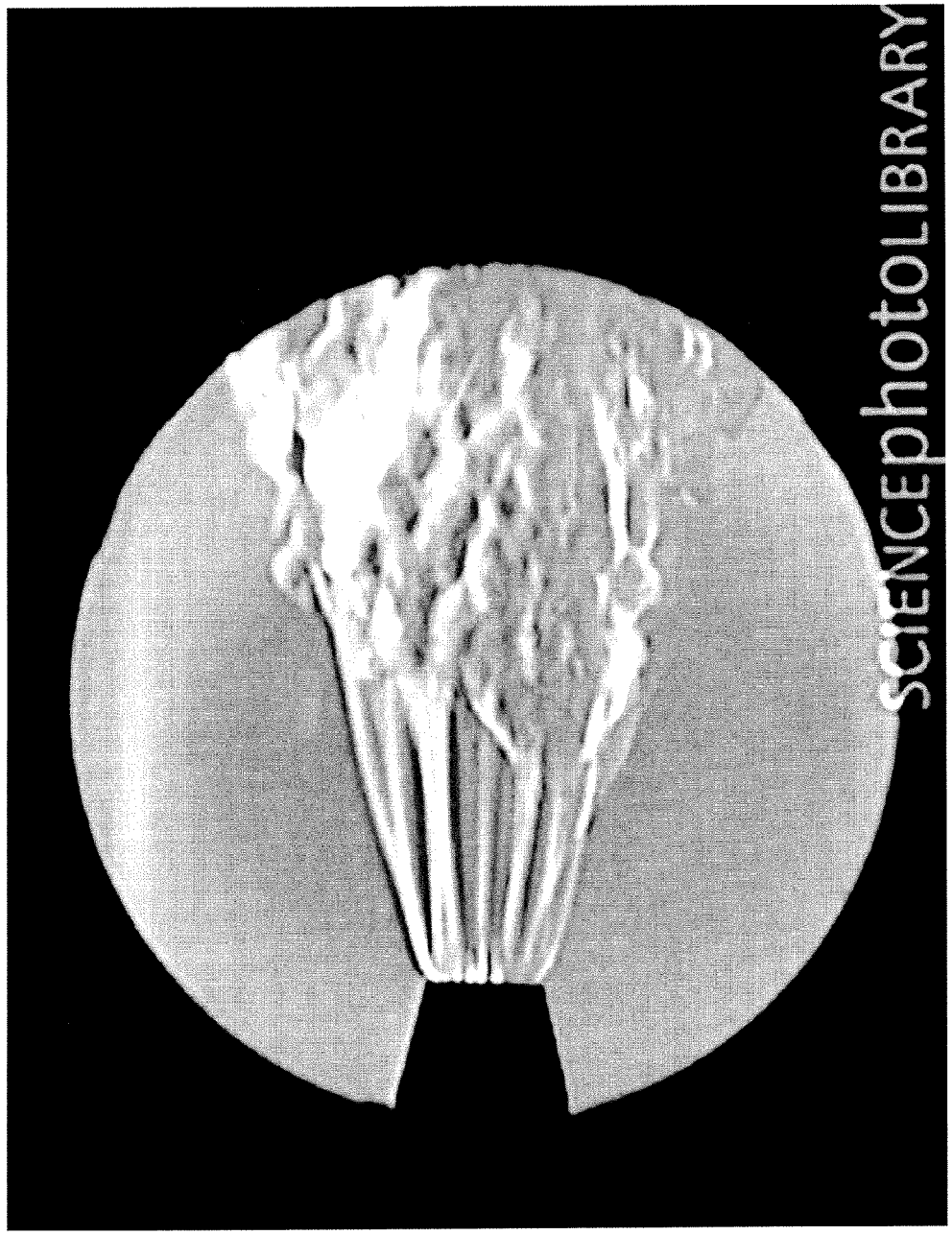
FIG. 11 is a computer-enhanced Schlieren Photography image showing "free-jet" expansion of gases and visualizing the Joule-Thomson (Kelvin) Effect.
Figure 12:
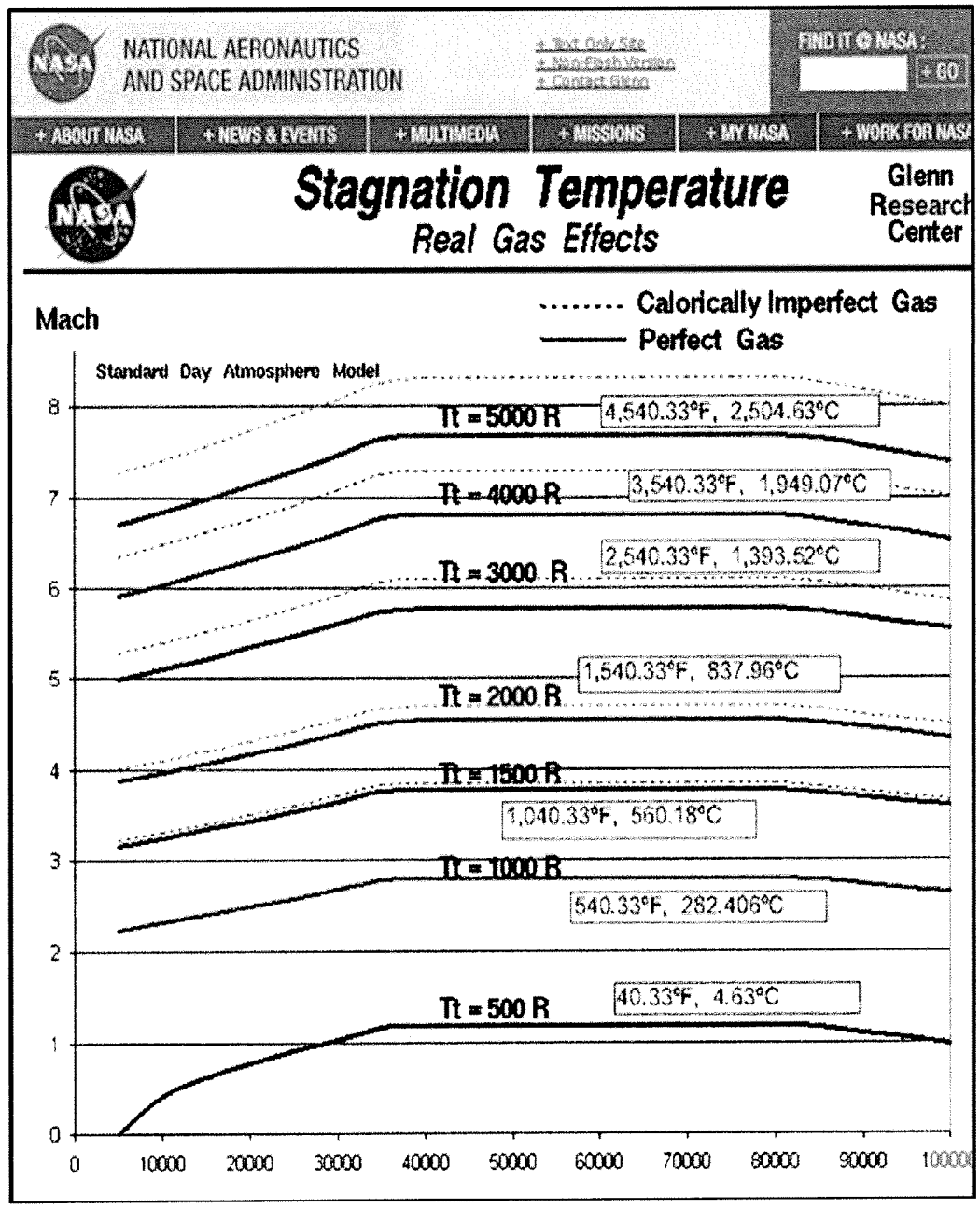
FIG. 12 is a Graphic Table Illustration (Stagnation Temperature) provided by the U.S. NASA showing the Stagnation Temperature delivered at the collision-impact of various Mach-speed collisions of perfect and imperfect gases.
Figure 13:
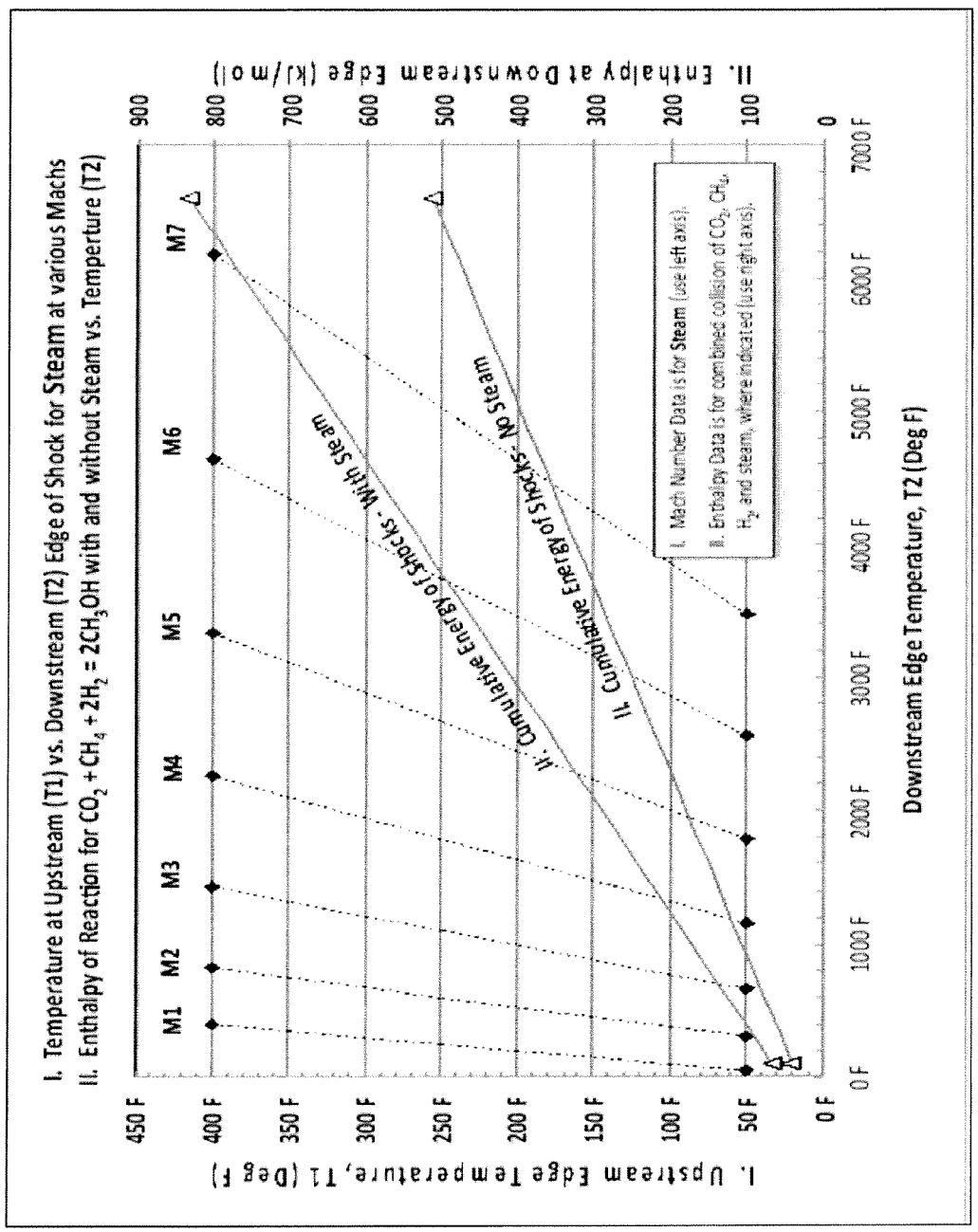
FIG. 13 is a Graphic Table Illustration showing various Mach-Speed Stagnation Temperatures, Collision Energy and Enthalpy of Gaseous Reactants (comprising $CO_2$, $H_2$, and $CH_4$) with Steam and without Steam.

Hess's Law predicts and explains the stability of the resulting enthalpy state for all reactants. These are the building blocks and this is the way to further design and construct Butane and Octane as either intermediates or as end-products and for making liquid fuel in the most-efficient way while using and recycling the industrially captured $CO_2$. In general, for those who are skilled in the art, the practical application is the enabling power and "energy-and-mass transfer" shockwave reaction mechanism to design long-chain hydrocarbon and other chemical compounds following the afore-mentioned steps, which can be shown in the generalized equation, below:

$$C_nH_x+C_nH_x+nH_2+[\text{CHONPS}]+\text{SRM}$$
Any→Designer's Long-Chain Hydrocarbon, or Liquid Fuels or Chemical Compounds, including pharmaceuticals, biochemicals and medicines [See: FIG. 10]

The "CHONPS" used herein is intended to illustrate the entire range of "designer reactants" that could be used inside the SRM to make a "designer compound". CHONPS is a mnemonic for the main elements that occur naturally in living systems: any Carbon, Hydrogen, Oxygen, Nitrogen, Phosphorus, or Sulfur. For examples: any organic, inorganic, mineral or metallic chemical or compound, including combination-complexes, involving any Carbon, Hydrogen, Oxygen, Nitrogen, Phosphorus, Sulfur or water itself, can all be used.

It is to be noted, for an example, that Ethylene or Propylene can be made in the SRM by collision of Methane gas ($CH_4$) with pure Carbon C (such as from either black soot, black char from pet coke, or from graphite) when engineered with a balanced supply of $H_2$ gas and sufficient shock energy. For the purposes of illustrating this invention, the Applicant elects to discuss the "building block steps" of making Ethylene from industrially captured $CO_2$ (such as from post-combustion emission or from pre-combustion Natural Gas component) because it has the merit of greater social good and overall conservation of matter and energy consumption, and most importantly it reduces the Greenhouse Gas effect on the environment and can help to provide a practical worldwide solution for captured $CO_2$.

The terms and expressions which have been employed are used as terms of description and not as terms of limitation, and there is no intention, in the use of such terms and expressions, of excluding any equivalents of the features shown and described or portions thereof, but it is recognized that various modifications are possible within the scope of the invention claimed.

REFERENCES

The following references, to the extent that they provide exemplary procedural or other details supplementary to those set forth herein, are specifically incorporated herein by reference.

PATENT DOCUMENTS

U.S. Pat. No. 6,706,770
U.S. Pat. No. 7,842,264

What is claimed is:

1. A process for the production of chemical products employing supersonic shockwaves comprising
pressurizing a first compressible fluid reactant;
passing said first compressible fluid reactant through a first supersonic nozzle so as to produce a first supersonic jet, wherein said first supersonic nozzle is configured to inject said first compressible fluid reactant, at Mach speeds in the range of Mach 3 to Mach 8, wherein said first supersonic jet contain shockwaves extending beyond an exit end of said first supersonic nozzle;
pressurizing a second compressible fluid reactant;
passing said second compressible fluid reactant through a second supersonic nozzle so as to produce a second supersonic jet, wherein said second supersonic nozzle is configured to inject said second compressible fluid reactant, at Mach speeds in the range of Mach 3 to Mach 8, wherein said second supersonic jet contains shockwaves extending beyond an exit end of said second supersonic nozzle,
wherein said first and second supersonic nozzles are positioned within an injection tube in opposing relationship so that axes of said first and said second nozzles intersect with each other to form a localized reaction zone within said injection tube in a region where said first supersonic jet and said second supersonic jet collide and interact with said shockwaves,
wherein each of said first compressible fluid reactant and said second compressible fluid reactant is selected from the group consisting of a gas, a hydrocarbon, water, steam, sulfur, phosphorus, dichloroethane, methanol, ethanol, and mixtures thereof, wherein the gas is selected from the group consisting of hydrogen, oxygen, nitrogen, carbon monoxide, carbon dioxide, chlorine, hydrogen chloride, and mixtures thereof, and
whereby temperature and pressure are raised in at least portions of said localized reaction zone by means of the collisions and interaction with said shockwaves, and rapid endothermic chemical reactions between said first compressible fluid reactant and said second compressible fluid reactant occur followed by rapid exothermic reactions and adiabatic cooling to produce a chemical product.

2. The process in accordance with claim 1 wherein said first compressible fluid reactant is vaporized methanol, said second compressible fluid reactant is vaporized methanol, the angle between the axes of said first and second supersonic nozzles is substantially 180 degrees, and said chemical product is ethanol and water.

3. The process in accordance with claim 1 wherein said first compressible fluid reactant comprises a mixture of at least two compressible fluid reactants.

4. The process in accordance with claim 1 wherein both said first and second compressible fluid reactants comprise a mixture of at least two compressible fluid reactants.

5. The process in accordance with claim 1 wherein a compressible fluid reactant is steam.

6. The process in accordance with claim 1, further comprising:
pressurizing a first compressible fluid,
passing said first compressible fluid and a first liquid reactant through a first two-fluid nozzle to produce a first jet containing fine droplets of said first liquid reactant,
wherein said first two-fluid nozzle and the axes of said first and second supersonic nozzles intersect with each other in said localized reaction zone within said injection tube where said first jet containing fine droplets of said first liquid reactant collides with said first and said second supersonic jets and interacts with said shockwaves,
whereby temperature and pressure are raised in at least a portion of said localized reaction zone by means of said collisions and interactions with said shockwaves and rapid chemical reactions occur among said droplets of said first liquid reactant and said first and said second compressible fluid reactants to produce a chemical product.

7. The process in accordance with claim 6, further comprising:
pressurizing a second compressible fluid,
passing said second compressible fluid and a second liquid reactant through a second two-fluid nozzle to produce a second jet containing fine droplets of said second liquid reactant,
wherein said second two-fluid nozzle is positioned within said injection tube so that the axis of said second two-fluid nozzle intersects the axes of said first two-fluid nozzle and said first and second supersonic nozzles within said localized reaction zone where said first and said second jets containing fine droplets of said first and second liquid reactants collide with said first and said second supersonic jets and interact with said shockwaves,
whereby temperature and pressure are raised in at least a portion of said localized reaction zone by means of said collisions and interactions with said shockwaves and rapid chemical reactions occur among said first and said second fine liquid droplets of said first and second liquid reactants and said first and said second compressible fluid reactants to produce a chemical product.

8. The process in accordance with claim 6 wherein a compressible fluid is steam.

9. The process in accordance with claim 7 where a compressible fluid is steam.

10. The process in accordance with claim 6 wherein said first liquid reactant comprises a mixture of at least two liquid reactants.

11. The process in accordance with claim 6 wherein said first compressible fluid reactant comprises a mixture of at least two compressible fluid reactants.

12. The process in accordance with claim 1 further comprising:
pressurizing a third compressible fluid reactant;
passing said third compressible fluid reactant through a third supersonic nozzle so as to produce a third supersonic jet containing shockwaves extending beyond an exit end of said third supersonic nozzle,
wherein the third supersonic nozzle is positioned within the injection tube so that an axis of said third supersonic nozzle intersects with the axes of said first and said second supersonic nozzles in the localized reaction zone within said injection tube in a region where said first supersonic jet, said second supersonic jet, and said third supersonic jet collide and interact with said shockwaves,
wherein said first and second supersonic nozzles are positioned within an injection tube in opposing relationship so that axes of said first and said second nozzles intersect with each other to form a localized reaction zone within said injection tube in a region where said first supersonic jet and said second supersonic jet collide and interact with said shockwaves,
wherein each of said first compressible fluid reactant and said second compressible fluid reactant is selected from the group consisting of a gas, a hydrocarbon, water, steam, sulfur, phosphorus, dichloroethane, methanol, ethanol, and mixtures thereof, wherein the gas is selected from the group consisting of hydrogen, oxygen, nitrogen, carbon monoxide, carbon dioxide, chlorine, hydrogen chloride, and mixtures thereof, and
whereby temperature and pressure are raised in at least portions of said localized reaction zone by means of said collisions and interaction with said shockwaves, and rapid endothermic chemical reactions between said first compressible fluid reactant, said second compressible fluid reactant, and said third compressible fluid reactant occur followed by rapid exothermic chemical reactions and adiabatic cooling to produce a chemical product.

13. The process in accordance with claim 12 wherein said first compressible fluid reactant is carbon dioxide, said second compressible fluid reactant is methane and said third compressible fluid reactant is hydrogen, said chemical product is methanol, and the molar ratio of said reactants and said chemical product is, respectively, 1:1:2→2.

14. The process in accordance with claim 12 wherein said first compressible fluid reactant is carbon dioxide, said second compressible fluid reactant is methane and said third compressible fluid reactant is hydrogen, said chemical product is ethane and water, and the molar ratio of said reactants and said product is, respectively, 1:1:3→1:2.

15. The process in accordance with claim 12 wherein an angle between the axes of the said first and said second supersonic nozzles is substantially 180 degrees and an angle between the axis of said third supersonic nozzle and said first or second supersonic nozzle is substantially 90 degrees.

16. The process in accordance with claim 12 wherein a compressible fluid reactant is steam.

17. The process in accordance with claim 12 further comprising:
pressurizing a fourth compressible fluid reactant;
passing said fourth compressible fluid reactant through a fourth supersonic nozzle so as to produce a fourth supersonic jet containing shockwaves extending beyond an exit end of said fourth supersonic nozzle, wherein the fourth supersonic nozzle is positioned within the injection tube so that an axis of said fourth supersonic nozzle intersects with the axes of said first, said second, and said third supersonic nozzles in the localized reaction zone within said injection tube in a region where said first supersonic jet, said second supersonic jet, said third supersonic jet, and said fourth supersonic jet collide and interact with said shockwaves, wherein said first and second supersonic nozzles are positioned within an injection tube in opposing relationship so that axes of said first and said second nozzles intersect with each other to form a localized reaction zone within said injection tube in a region where said first supersonic jet and said second supersonic jet collide and interact with said shockwaves, wherein each of said first compressible fluid reactant and said second compressible fluid reactant is selected from the group consisting of a gas, a hydrocarbon, water, steam, sulfur, phosphorus, dichloroethane, methanol, ethanol, and mixtures thereof, wherein the gas is selected from the group consisting of hydrogen, oxygen, nitrogen, carbon monoxide, carbon dioxide, chlorine, hydrogen chloride, and mixtures thereof, and whereby temperature and pressure are raised in at least portions of said localized reaction zone by means of said collisions and interaction with said shockwaves, and rapid endothermic chemical reactions between said first compressible fluid reactant, said second compressible fluid reactant, said third compressible fluid reactant, and said fourth compressible fluid reactant occur followed by rapid exothermic chemical reactions and adiabatic cooling to produce a chemical product.

18. The process in accordance with claim 17 wherein said first compressible fluid reactant is carbon dioxide, said second compressible fluid reactant is methane, said third compressible fluid reactant is hydrogen, and said fourth compressible fluid reactant is chlorine, said chemical product is dichloroethane and water, and the molar ratio of said reactants and said product is, respectively, 1:2:1→1:2.

* * * * *